(12) United States Patent
Weaver et al.

(10) Patent No.: US 11,014,078 B2
(45) Date of Patent: May 25, 2021

(54) METHOD FOR THE SYNTHESIS AND ISOLATION OF FACIAL-TRIS-HOMOLEPTIC PHENYLPYRIDINATO IRIDIUM (III) PHOTOCATALYSTS

(71) Applicant: The Board of Regents for Oklahoma State University, Stillwater, OK (US)

(72) Inventors: Jimmie Dean Weaver, Stillwater, OK (US); Kip Allen Teegardin, Glencoe, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 0 days.

(21) Appl. No.: 16/491,710

(22) PCT Filed: Mar. 6, 2018

(86) PCT No.: PCT/US2018/021112
§ 371 (c)(1),
(2) Date: Sep. 6, 2019

(87) PCT Pub. No.: WO2018/165134
PCT Pub. Date: Sep. 13, 2018

(65) Prior Publication Data
US 2020/0376474 A1    Dec. 3, 2020

Related U.S. Application Data

(60) Provisional application No. 62/467,594, filed on Mar. 6, 2017.

(51) Int. Cl.
| | | |
|---|---|---|
| *B01J 31/18* | (2006.01) | |
| *B01J 35/00* | (2006.01) | |
| *B01J 37/00* | (2006.01) | |
| *B01J 37/04* | (2006.01) | |
| *B01J 37/06* | (2006.01) | |
| *B01J 37/10* | (2006.01) | |
| *C07F 15/00* | (2006.01) | |

(52) U.S. Cl.
CPC .......... *B01J 31/181* (2013.01); *B01J 35/004* (2013.01); *B01J 37/009* (2013.01); *B01J 37/04* (2013.01); *B01J 37/06* (2013.01); *B01J 37/10* (2013.01); *C07F 15/0033* (2013.01); *B01J 2231/005* (2013.01); *B01J 2531/827* (2013.01)

(58) Field of Classification Search
CPC ... B01J 31/18; B01J 35/00; B01J 37/00; B01J 37/04; B01J 37/06; B01J 37/10
See application file for complete search history.

(56) References Cited

U.S. PATENT DOCUMENTS

| | | | |
|---|---|---|---|
| 3,549,649 A | 12/1970 | Ritchie et al. | |
| 7,790,888 B2 * | 9/2010 | Bold | .................. C07F 15/0033 546/2 |
| 9,029,541 B2 * | 5/2015 | Fujimura | ............... H05B 33/14 546/4 |

OTHER PUBLICATIONS

International Search Report, dated May 14, 2018, in PCT/US2018/21112, filed Mar. 6, 2018.
Written Opinion of the International Searching Authority, dated May 14, 2018, in PCT/US2018/21112, filed Mar. 6, 2018.
Rollema, et al.; "In Vivo Intracerebral Microdialysis Studies in Rats of MPP+ Analogues and Related Charged Species," Journal of Medicinal Chemistry (1990), vol. 33, No. 8, pp. 2221-2230.

* cited by examiner

*Primary Examiner* — D Margaret M Seaman
(74) *Attorney, Agent, or Firm* — Dunlap Codding, P.C.

(57) ABSTRACT

Methods of synthesizing and isolating facial-tris-homoleptic phenylpyridinato iridium (III) photocatalysts are disclosed. Also disclosed are methods of recovering excess 2-phenylpyridine ligands from said syntheses.

20 Claims, 26 Drawing Sheets
(15 of 26 Drawing Sheet(s) Filed in Color)

FIG. 10

*Fac*-tris(2-phenylpyridinato) iridium(III) – ¹H NMR 2-phenylpyridine - ¹H NMR 2-phenylpyridine – ¹³C NMR

*Fac*-tris(2-(4,6-difluorophenyl)pyridinato) iridium(III) $^1$H NMR

Fac-tris(2-(4,6-difluorophenyl)pyridinato)iridium(III) - ¹⁹F NMR

Fac-tris(2-(4,6-difluorophenyl)pyridinato)iridium(III) - ¹³C NMR 2-(4,6-Difluoro)phenylpyridine - ¹H NMR 2-(4,6-Difluoro)phenylpyridine - ¹⁹F NMR FIG. 20 2-(4,6-Difluoro)phenylpyridine - $^{13}C$ NMR Fac-Tris[5-fluoro-2-(2-pyridinyl-N)phenyl-C]iridium(III)) - ¹H NMR Fac-Tris[5-fluoro-2-(2-pyridinyl-N)phenyl-C]iridium(III) - $^{19}F$ NMR Fac-Tris[2-(2-pyridinyl-N)-5-(trifluoromethyl)phenyl-C]iridium(III) - ¹H NMR

*Fac*-Tris[2-(2-pyridinyl-N)-5-(trifluoromethyl)phenyl-C]iridium(III) - ¹⁹F NMR

Tris [2-(2-pyridinyl-N)-5-(tert-butyl)phenyl-C]iridium(III) - ¹H NMR

Tris [2-(2-pyridinyl-N)-5-(tert-butyl)phenyl-C]iridium(III) - ¹³C NMR

METHOD FOR THE SYNTHESIS AND ISOLATION OF FACIAL-TRIS-HOMOLEPTIC PHENYLPYRIDINATO IRIDIUM (III) PHOTOCATALYSTS

CROSS REFERENCE TO RELATED APPLICATIONS/INCORPORATION BY REFERENCE STATEMENT

This application is a U.S. National Stage Application filed under 35 U.S.C. § 371 of International Application No. PCT/US2018/21112, filed Mar. 6, 2018; which claims benefit under 35 U.S.C. 119(e) of U.S. Provisional Application Ser. No. 62/467,594, filed Mar. 6, 2017, the entirety of which is hereby expressly incorporated herein by reference.

STATEMENT REGARDING FEDERALLY SPONSORED RESEARCH OR DEVELOPMENT

This invention was made with Government support under Grant No. 5R01GM115697-02 awarded by the National Institutes of Health. The Government has certain rights in the invention.

BACKGROUND

For more than 30 years, transition metal complexes have been known to mediate single-electron transfers (SET) and have led to SET-initiated polymerization reactions (Lalevee et al., 2011), dye-sensitized solar cells (Kalyanasundaram et al., 1998), and light emitting diodes (Lowry et al., 2006). Despite the substantial use of transition metal mediated-SET in these applications and processes, application towards synthetic organic chemistry has been sporadic and relatively infrequent (Pac et al., 1981; Cano-Yelo et al., 1984; and Narayanam et al., 2011) until more recently. Early reports of transition metal-based photocatalytic mediated organic transformations utilized Ru-based photocatalysts such as tris-(2,2'-bipyridine) ruthenium (II) or Ru(bpy)$_3$$^2$+, which when excited by visible light undergoes a metal to ligand charge transfer (MLCT) and facilitates one-electron oxidation or reduction of the complex (McCusker, 2003). King et al. (1985) reported the synthesis and characterization of the neutral fac-tris-phenylpyridinato iridium (III), (Ir(ppy)$_3$) photocatalyst. In general, the neutral Ir-photocatalysts tend to be substantially more reducing photocatalysts than their cationic counterparts from both the excited state and the reduced ground state, and thus are a complimentary class of photocatalysts, but it was not until 2012 that they were used (Nguyen et al., 2012).

Pac et al. (1981) utilized Ru(bpy)$_3$Cl$_2$ in one of the first reports of small organic molecule activation by this complex, in which they reported the reduction of electron deficient alkenes using a stoichiometric reductant. Fukuzumi et al. (1990) also described reductive dehalogenation of phenacyl bromide utilizing this complex. More recently, Nicewicz et al. (2008) reported direct asymmetric alkylation of aldehydes, and Ischay et al. (2008) reported [2+2] cycloadditions of enones, both utilizing Ru(bpy)$_3$Cl$_2$, thereby modernizing transition metal photochemistry. Over the last few years, the number of reported organic transformations that utilize transition metal photocatalyst has increased steadily.

During the last eight years, the neutral tris-homoleptic Ir-complexes have also grown in importance (Prier et al., 2013). Accordingly, Nguyen et al. (2012) reported an efficient hydrodeiodination of alkyl, alkenyl, and aryl iodides using Ir(ppy)$_3$. Zuo et al. (2014) investigated several neutral complexes—Ir(p-F-ppy)$_3$, Ir(dFppy)$_3$, Ir[p-F(t-Bu)-ppy]$_3$, and Ir[dF(t-Bu)-ppy]$_3$—which all out performed Ir(ppy)$_3$ in the decarboxylative arylation of alpha amino acids. Recently the inventors (Weaver et al., 2014; Singh et al., 2013; Singh et al., 2014; Senaweera et al., 2014; and Singh et al., 2015) as well as other groups (Prier et al., 2013) have utilized the fac-tris-homoleptic iridium (III) complexes, which have proven to perform a series of other powerful transformations with high catalytic efficiencies. An exemplary (but non-limiting) list of transformations and reactions performed by the neutral fac-tris homoleptic complexes is shown below:

decarboxylative alkylation of amino acids (Zuo et al., 2014);

decarboxylative alkylation (addition to Michael acceptors) (Chu et al., 2014);

alpha alkylation of aldehydes (Terrett et al., 2014);

coupling of tertiary amines and 2-chloroazoles (Singh et al., 2013);

alkylation of 2-bromoazoles (Arora et al., 2015);

hydrodefluorination (Senaweera et al., 2014);

E-Z isomerization of alkenes (Singh et al., 2014);

photocatalytic C-F alkylation (Singh et al., 2015);

functionalization of ligands (Devery et al., 2015);

alkyl iodide free radical reactions (Nguyen et al., 2012); and visible light-mediated atom transfer radical additions (Wallentin et al., 2012).

Despite the rapidly increasing utility of the homoleptic iridium (III) complexes in organic syntheses, only a few are commercially available. There are a number of reported synthetic methods that use Ir(acac)$_3$ (see, for example, Dedeian et al., 1991; Tamayo et al., 2003; Lee et al., 2007; and Tsuboyarna et al., 2003), which is a more expensive Ir (III) source, or methods that alternatively require two steps. The first step results in the formation of a chloro-bridging dimer via coordination of two phenylpyridine ligands. Then, in a subsequent step, the halogen is extracted, often aided by silver, and a third phenylpyridine is added via cyclometalation (McDonald et al., 2008; and Tamayo et al., 2003). Even in the case of the tris-homoleptic cyclometalated complexes, this two-step sequence is commonly employed. Ideally, one could hope to place all three bidentate ligands in the same reaction to generate the thermodynamically favored facial-homoleptic iridium (III) complex. It has been known that the meridional homoleptic iridium (III) complex is the kinetically favored product, but the facial complex can be obtained at temperatures greater than 200° C. and is the thermodynamically favored product (Tamayo et al., 2003).

Konno et al. (2003) reported microwave synthesis of tris-cyclometalated iridium complexes, but this synthesis required a large excess of ligand (50 to 100 equivalents), which limits the scope of the reaction to readily available ligands. Perhaps more importantly, the scale of the reaction is limited by the microwave equipment used.

In Singh et al. (2015), the inventors disclosed a simple, reliable, and straightforward preparation method that would allow for the acquisition of the facial-homoleptic iridium complexes in high yields via a selective one step process starting with the least expensive source of Ir(III), IrCl$_3$*nH$_2$O and that used water as the only solvent (FIG. 1). However, while the methods of Singh et al. can be used to make gram scale quantities of these complexes, there are some notable shortcomings. Namely, purification of the complexes via the method of Singh et al. require at least one column chromatography step, and this step is time intensive and requires copious amounts of organic solvents; this step is particularly challenging, because of the low solubility of these complexes. Indeed, the isolation of the complex is often more challenging than its synthesis. In addition, the methods of Singh et al. do not allow for the recovery of excess ligand.

Therefore, there is a need in the art for new and improved methods of synthesis and isolation of facial-homoleptic iridium complexes that yield a high purity of complex on a gram scale and that allow for recovery of excess ligand. It is to such new and improved methods that the present disclosure is directed.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 10 contains $^1H$ NMR spectra of Fac-Tris(2-phenylpyridinato) iridium(III), as produced in Example 3.

DETAILED DESCRIPTION

Figure 1:
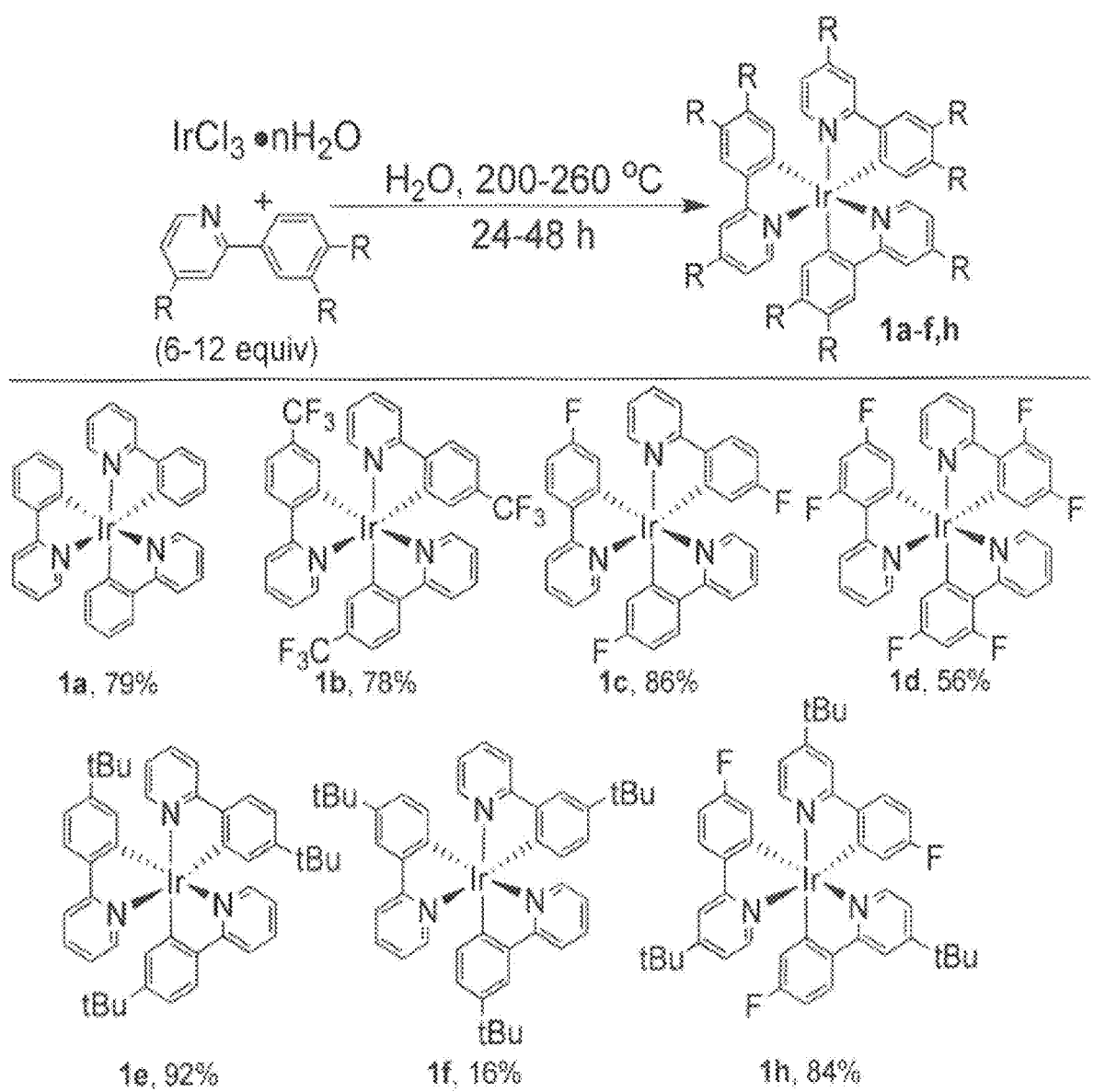
FIG. 1 illustrates a prior art approach to acquiring the facial-homoleptic iridium complexes via a selective one step process that utilizes the least expensive source of Ir(III), $IrCl_3 \cdot nH_2O$, and that utilizes water as the only solvent.

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses and chemical analyses.

All patents, published patent applications, and non-patent publications mentioned in the specification are indicative of the level of skill of those skilled in the art to which this presently disclosed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed herein can be made and executed without undue experimentation in light of the present disclosure. While the compositions and methods of the inventive concept(s) have been described in terms of particular embodiments, it will be apparent to those of skill in the art that variations may be applied to the compositions and/or methods and in the steps or in the sequence of steps of the methods described herein without departing from the concept, spirit, and scope of the inventive concept(s). All such similar substitutions and modifications apparent to those skilled in the art are deemed to be within the spirit, scope, and concept of the inventive concept(s) as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. For example, the term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

As used herein, "substantially pure" means an object species is the predominant species present (i.e., on a molar basis it is more abundant than any other individual species in the composition), and a substantially purified fraction is a composition wherein the object species comprises at least about 50 percent (on a molar basis) of all macromolecular species present. Generally, a substantially pure composition will comprise more than about 80 percent of all macromolecular species present in the composition, such as (but not limited to) more than about 85%, 90%, 95%, and 99%. In a particular (but non-limiting) embodiment, the object species is purified to essential homogeneity (contaminant species cannot be detected in the composition by conventional detection methods), wherein the composition consists essentially of a single macromolecular species.

Turning now to the inventive concept(s), certain non-limiting embodiments of the present disclosure are directed to a method of synthesizing and isolating Iridium-based photocatalysts that yield a high purity of photocatalyst, wherein the photocatalyst can be produced on, for example but not by way of limitation, at least a gram scale, and wherein the method also allows for recovery of excess ligand. Ir-based photocatalysts have revolutionized synthetic organic chemistry in the last 10 years, vastly increasing the types of chemical transformations that are possible. Certain non-limiting embodiments of the present disclosure are related to the synthesis of the photocatalysts themselves, which is notoriously difficult and costly. The difficulty in catalyst synthesis and isolation has prevented broad access to this class of photocatalyst and consequently limited potential chemistry that could be developed. Herein is provided an improved method of synthesis and isolation that allows yields of up to 99% of the desired photocatalyst without the need for chromatography as a purification method. In addition, excess ligand is recovered in high yield. Also, the methods disclosed herein produce isolated photocatalysts at a cost that is about an order of magnitude less than prior art methods.

In certain non-limiting embodiments, the present disclosure includes a method of synthesizing and isolating a facial-tris-homoleptic phenylpyridinato iridium (III) photocatalyst. The method may include one or more of the following steps (note that the steps may be performed in any order, and the alphabetical and/or numerical designation of same is for purposes of illustration only):

(a) charging a reactor with $IrCl_3*nH_2O$ and a 2-phenylpyridine ligand to form a reaction mixture;
(b) pressurizing the reaction mixture with inert gas;
(c) heating the reaction mixture for a sufficient amount of time to synthesize a fac-tris-homoleptic phenylpyridinato iridium (III) photocatalyst;
(d) cooling the reaction mixture;
(e) removing the reaction mixture from the reactor, wherein the reaction mixture comprises a solid material and an aqueous phase; and
(f) isolating the fac-tris-homoleptic phenylpyridinato iridium (III) photocatalyst from the reaction mixture, wherein the isolation process comprises performing two or more of the following steps: (I) contacting the reaction mixture with an organic solvent; (II) extracting the fac-tris-homoleptic phenylpyridinato iridium (III) photocatalyst into the organic solvent; (III) separating at least a portion of an organic phase from an aqueous phase; (IV) filtering the separated organic phase; (V) drying the separated organic phase containing the fac-tris-homoleptic phenylpyridinato iridium (III) photocatalyst to form a drying reagent; and (VI) removing organic solvent from the drying reagent (such as, but not limited to, by evaporation). The fac-tris-homoleptic phenylpyridinato iridium (III) photocatalyst is isolated with a purity of at least about 90%, and the at least about 90% purity of the photocatalyst is obtained in the absence of any chromatography steps.

In certain particular (but non-limiting) embodiments, the isolation process of step (f) comprises performing three or more of steps (I)-(VI), such as (but not limited to), four or more of steps (I)-(VI), five or more of steps (I)-(VI), or all of steps (I)-(VI).

In certain non-limiting embodiments, at least about 1.0 g of the fac-tris-homoleptic phenylpyridinato iridium (III) photocatalyst is isolated by the above method.

Any reactor known in the art or otherwise contemplatable by a person of ordinary skill in the art that is capable of withstanding the temperature and pressure conditions utilized in the disclosed synthesis methods may be used as the reactor in accordance with the present disclosure. For example, but not by way of limitation, the reactor may be a Parr reactor.

Any iridium (III) chloride capable of reacting with ligand to form photocatalyst in accordance with the methods disclosed or otherwise contemplated herein can be utilized as $IrCl_3*nH_2O$ in accordance with the present disclosure. For example (but not by way of limitation), in the formula $IrCl_3*nH_2O$, n may be 0 (i.e., anhydrous $IrCl_3$). Alternatively, n may be any positive number (i.e., an iridium (III) chloride hydrate).

Any 2-phenylpyridine ligand known in the art or otherwise contemplatable by a person of ordinary skill in the art may be utilized in accordance with the present disclosure. For example (but not by way of limitation), any of the 2-phenylpyridine ligands depicted in the FIGS. 1, 2, 8, 12-13, 18-20, and 27, as well as any of the 2-phenylpyridine ligands that would produce any of the phenylpyridinato iridium (III) complexes 1a-1f and 1h depicted in FIG. 1, or any of the complexes depicted in FIGS. 2, 5-11, 14-17, and 21-28, may be utilized in accordance with the present disclosure. However, these structures are provided solely for purposes of illustration only, and it will be understood by a person of ordinary skill in the art that other 2-phenylpyridine ligands may be utilized in accordance with the present disclosure. Particular non-limiting examples of 2-phenylpyridine ligands that may be utilized include 2-phenylpyridine, 2-(2,4-difluorophenyl)pyridine, 2-(4,6-difluorophenyl)pyridine, 2-(4-(trifluoromethyl)phenyl)pyridine, 2-(4-fluorophenyl)pyridine, 2-(4-(tert-butyl)phenyl)pyridine, 2-(3-(tert-butyl)phenyl)pyridine, 4-(tert-butyl)-2-(4-fluorophenyl)pyridine, and the like.

In a particular (but non-limiting) embodiment, the 2-phenylpyridine ligand is 2-phenylpyridine, and the photocatalyst produced by the method is $Ir(ppy)_3$. In another particular (but non-limiting) embodiment, the 2-phenylpyridine ligand is 2-(2,4-difluorophenyl)pyridine, and the photocatalyst produced by the method is $Ir(dFppy)_3$.

In certain non-limiting embodiments, the $IrCl_3*nH_2O$ and the 2-phenylpyridine ligand are reacted in the presence of DI water.

In the method, the $IrCl_3*nH_2O$ is reacted with an excess of the 2-phenylpyridine ligand. For example, 1 equivalent of $IrCl_3*nH_2O$ may be reacted with at least three or more equivalents of 2-phenylpyridine ligand. In particular, 1 equivalent of $IrCl_3*nH_2O$ may be reacted with at least three, four, five, six, seven, eight, nine, ten, eleven, twelve, thirteen, fourteen, fifteen, sixteen, seventeen, eighteen, nineteen, twenty, 25, 30, 35, 40, 45, 50, 55, 60, or more equivalents of 2-phenylpyridine ligand (as well as any value between any two of these numbers). In a particular (but non-limiting) embodiment, 1 equivalent of $IrCl_3*nH_2O$ is reacted with 12 equivalents of 2-phenylpyridine ligand.

Any inert gas may be utilized to pressurize the reactor. Examples of inert gases that may be utilized in accordance with the present disclosure include (but are not limited to) argon gas and nitrogen gas ($N_2$).

In certain non-limiting embodiments, step (b) above is further defined as pressurizing and depressurizing the reactor containing the reaction mixture at least two times with inert gas, then charging the reactor with inert gas prior to proceeding to step (c). Any number of pressurizing and depressurizing steps may be utilized in accordance with the present disclosure, including (but not limited to), two times, three times, four times, five times, six times, seven times, eight times, nine times, ten times 15 times, 20 times, 25 times, 30 times, etc.

Regardless of the number of pressurizations used, the reactor may be pressurized in each pressurization step to a pressure that allows the method to function as described herein. In one non-limiting embodiment, the reactor is pressurized to a pressure in a range of from about 10 psi to about 30 psi. However, it is to be understood that these exemplary pressures are non-limiting, and any pressures known in the art as capable for use with a reactor as described herein also fall within the scope of the present disclosure.

The reaction mixture may be heated to any temperature, and held at that temperature for any time period, that allows for synthesis of the photocatalysts in accordance with the present disclosure. Ideally, the heating temperatures and times should also allow for recovery of excess ligand from the reactor. However, this is not an explicit requirement of the present disclosure.

In a particular (but non-limiting) embodiment, the reaction mixture is heated to a temperature in a range of from about 200° C. to about 260° C. for a time period in a range of from about 24 hours to about 48 hours. However, it is to be understood that temperatures and times above and below these ranges may be utilized in accordance with the present disclosure.

Following the heating step, the reaction mixture is cooled to a temperature at which the following steps can be performed. In a particular (but non-limiting) embodiment, the reaction mixture is cooled to room temperature. The term "room temperature," as utilized herein, refers to a temperature typically in a range of from about 20° C. to about 25° C., such as (but not limited to) 21° C. to about 23° C., and including (but not limited to) about 22° C.

Any organic solvent(s) or solutions thereof known in the art or otherwise contemplated herein may be utilized in accordance with the present disclosure, so long as the photocatalysts synthesized by the methods of the present disclosure are partially or fully soluble therein. For example (but not by way of limitation), the organic solvent may comprise at least one of dichloromethane (DCM), acetone, and/or hexane.

The methods of the present disclosure may further include one or more steps that aid in increasing the yield of the photocatalyst product without requiring a chromatography step. For example (but not by way of limitation), the method may include the steps of washing the separated organic phase from step (f)(III) with an acidic solution, and then back extracting the acidic solution wash with organic solvent prior to performing the filtering step (f)(iv). In this step, the separated organic solvents from the various steps are combined prior to proceeding with the filtering step (f)(iv), and the acidic solution wash is combined with the aqueous phase for use in recovery of ligand. Any acidic solution capable of functioning in accordance with the method may be utilized; one non-limiting example thereof is an HCl solution.

Another non-limiting example of a step that may be included in the methods of the present disclosure to aid in increasing the yield of the photocatalyst product without requiring a chromatography step include the step of further extracting the aqueous phase separated in step (f)(III) with organic solvent and combining the separated, extracted organic phase with the organic phase separated in step (f)(III).

Another non-limiting example of a step that may be included in the methods of the present disclosure to aid in increasing the yield of the photocatalyst product without requiring a chromatography step include the step of (f)(VII) selectively extracting impurities from the drying reagent of (f)(VI) by washing with an organic solvent.

Certain non-limiting embodiments of the present disclosure include methods of synthesizing and isolating a facial-tris-homoleptic phenylpyridinato iridium (III) photocatalyst and recovering excess 2-phenylpyridine ligand from said synthesis. The method may include one or more of the following steps (note that the steps may be performed in any order, and the alphabetical and/or numerical designation of same is for purposes of illustration only):

(a) charging a reactor with $IrCl_3 \cdot nH_2O$ and a 2-phenylpyridine ligand to form a reaction mixture;
(b) pressurizing the reaction mixture with inert gas;
(c) heating the reaction mixture for a sufficient amount of time to synthesize a fac-tris-homoleptic phenylpyridinato iridium (III) photocatalyst;
(d) cooling the reaction mixture;
(e) removing the reaction mixture from the reactor, wherein the reaction mixture comprises a solid material and an aqueous phase;
(f) isolating the fac-tris-homoleptic phenylpyridinato iridium (III) photocatalyst from the reaction mixture, wherein the isolation process comprises performing two or more of the following steps: (I) contacting the reaction mixture with an organic solvent; (II) extracting the fac-tris-homoleptic phenylpyridinato iridium (III) photocatalyst into the organic solvent; (III) separating at least a portion of an organic phase from an aqueous phase; (IV) filtering the separated organic phase; and (V) drying the separated organic phase containing the fac-tris-homoleptic phenylpyridinato iridium (III) photocatalyst to form a drying reagent; and (VI) removing organic solvent from the drying reagent (such as, but not limited to, by evaporation); and wherein the fac-tris-homoleptic phenylpyridinato iridium (III) photocatalyst is isolated with a purity of at least about 90%, and wherein the at least about 90% purity of the photocatalyst is obtained in the absence of any chromatography steps; and
(g) recovering excess 2-phenylpyridine ligand, wherein the recovery process comprises performing two or more of the following steps: (i) basifying the aqueous phase separated in (III) to a pH wherein at least a portion of excess 2-phenylpyridine separates out of the aqueous phase; (ii) contacting the reaction mixture of (i) with an organic solvent; (iii) extracting the 2-phenylpyridine ligand into the organic solvent; (iv) separating at least a portion of an organic phase from an aqueous phase; (v) filtering the separated organic phase; and (vi) drying the separated organic phase containing excess 2-phenylpyridine ligand to form a drying reagent; and (vii) removing organic solvent from the drying reagent to isolate excess 2-phenylpyridine ligand (such as, but not limited to, by evaporation); and wherein the excess 2-phenylpyridine ligand is recovered in a yield of at least about 40%.

Any form of base known in the art or otherwise contemplated herein (such as, but not limited to, a solid base or liquid base) that is capable of increasing the pH of the aqueous phase to a pH wherein at least a portion of excess 2-phenylpyridine separates out of the aqueous phase may be utilized in accordance with the present disclosure. In certain particular (but non-limiting) embodiments, the aqueous phase is basified using a solid base, as the use of a solid base (such as, but not limited to, NaOH pellets or other base pellets) minimizes the aqueous volume into which the ligand may partition.

The aqueous phase may be basified to any pH, so long as at least a portion of excess 2-phenylpyridine separates out of the aqueous phase. In particular (but non-limiting) embodiments, the aqueous phase is basified to a pH in a range of from about pH 10 to about pH 12.

In certain non-limiting embodiments, at least about 1.0 g of the fac-tris-homoleptic phenylpyridinato iridium (III) photocatalyst is isolated by the above method.

In certain particular (but non-limiting) embodiments, the isolation process of step (f) comprises performing three or more of steps (I)-(VI), such as (but not limited to), four or more of steps (I)-(VI), five or more of steps (I)-(VI), or all of steps (I)-(VI).

In certain particular (but non-limiting) embodiments, the recovery process of step (g) comprises performing three or more of steps (i)-(vii), such as (but not limited to), four or more of steps (i)-(vii), five or more of steps (i)-(vii), six or more of steps (i)-(vii), or all of steps (i)-(vii).

In a particular (but non-limiting) embodiment, the isolation process of step (f) is further defined as comprising performing all of steps (I)-(VI), and the recovery process of step (g) is further defined as comprising performing all of steps (i)-(vii).

Any reactor known in the art or otherwise contemplatable by a person of ordinary skill in the art that is capable of withstanding the temperature and pressure conditions utilized in the disclosed synthesis methods may be used as the reactor in accordance with the present disclosure. For example, but not by way of limitation, the reactor may be a Parr reactor.

Any iridium (III) chloride capable of reacting with ligand to form photocatalyst in accordance with the methods disclosed or otherwise contemplated herein can be utilized as $IrCl_3*nH_2O$ in accordance with the present disclosure. For example (but not by way of limitation), in the formula $IrCl_3*nH_2O$, n may be 0 (i.e., anhydrous $IrCl_3$). Alternatively, n may be any positive number (i.e., an iridium (III) chloride hydrate).

Any 2-phenylpyridine ligand known in the art or otherwise contemplatable by a person of ordinary skill in the art may be utilized in accordance with the present disclosure. For example (but not by way of limitation), any of the 2-phenylpyridine ligands depicted in the FIGS. 1, 2, 8, 12-13, 18-20, and 27, as well as any of the 2-phenylpyridine ligands that would produce any of the phenylpyridinato iridium (III) complexes 1a-1f and 1h depicted in FIG. 1, or any of the complexes depicted in FIGS. 2, 5-11, 14-17, and 21-28, may be utilized in accordance with the present disclosure. However, these structures are provided solely for purposes of illustration only, and it will be understood by a person of ordinary skill in the art that other 2-phenylpyridine ligands may be utilized in accordance with the present disclosure. Particular non-limiting examples of 2-phenylpyridine ligands that may be utilized include 2-phenylpyridine, 2-(2,4-difluorophenyl)pyridine, 2-(4,6-difluorophenyl)pyridine, 2-(4-(trifluoromethyl)phenyl)pyridine, 2-(4-fluorophenyl)pyridine, 2-(4-(tert-butyl)phenyl)pyridine, 2-(3-(tert-butyl)phenyl)pyridine, 4-(tert-butyl)-2-(4-fluorophenyl)pyridine, and the like.

In a particular (but non-limiting) embodiment, the 2-phenylpyridine ligand is 2-phenylpyridine, and the photocatalyst produced by the method is $Ir(ppy)_3$. In another particular (but non-limiting) embodiment, the 2-phenylpyridine ligand is 2-(2,4-difluorophenyl)pyridine, and the photocatalyst produced by the method is $Ir(dFppy)_3$.

In certain non-limiting embodiments, the $IrCl_3*nH_2O$ and the 2-phenylpyridine ligand are reacted in the presence of DI water.

In the method, the $IrCl_3*nH_2O$ is reacted with an excess of the 2-phenylpyridine ligand. For example, 1 equivalent of $IrCl_3*nH_2O$ must be reacted with at least three or more equivalents of 2-phenylpyridine ligand. In particular (but not by way of limitation), 1 equivalent of $IrCl_3*nH_2O$ may be reacted with at least three, four, five, six, seven, eight, nine, ten, eleven, twelve, thirteen, fourteen, fifteen, sixteen, seventeen, eighteen, nineteen, twenty, 25, 30, 35, 40, 45, 50, 55, 60, or more equivalents of 2-phenylpyridine ligand (as well as any value between any two of these numbers and any range formed from two of these values (or any value therebetween)). In a particular (but non-limiting) embodiment, 1 equivalent of $IrCl_3*nH_2O$ is reacted with 12 equivalents of 2-phenylpyridine ligand.

Any inert gas may be utilized to pressurize the reactor, so long as the reactor is capable of functioning as disclosed herein. Examples of inert gases that may be utilized in accordance with the present disclosure include (but are not limited to) argon gas and nitrogen gas ($N_2$).

In certain non-limiting embodiments, step (b) above is further defined as pressurizing and depressurizing the reactor containing the reaction mixture at least two times with inert gas, then charging the reactor with inert gas prior to proceeding to step (c). Any number of pressurizing and depressurizing steps may be utilized in accordance with the present disclosure, including (but not limited to), two times, three times, four times, five times, six times, seven times, eight times, nine times, ten times 15 times, 20 times, 25 times, 30 times, etc.

Regardless of the number of pressurizations used, the reactor may be pressurized in each pressurization step to a pressure that allows the method to function as described herein. In one non-limiting embodiment, the reactor is pressurized to a pressure in a range of from about 10 psi to about 30 psi. However, it is to be understood that these exemplary pressures are non-limiting, and any pressures known in the art as capable for use with a reactor as described herein also fall within the scope of the present disclosure.

The reaction mixture may be heated to any temperature, and held at that temperature for any time period, that allows for synthesis of the photocatalysts in accordance with the present disclosure. Ideally, the heating temperatures and times should also allow for recovery of excess ligand from the reactor. However, this is not an explicit requirement of the present disclosure.

In a particular (but non-limiting) embodiment, the reaction mixture is heated to a temperature in a range of from about 200° C. to about 260° C. for a time period in a range of from about 24 hours to about 48 hours.

Following the heating step, the reaction mixture is cooled to a temperature at which the following steps can be performed. In a particular (but non-limiting) embodiment, the reaction mixture is cooled to room temperature. The term "room temperature," as utilized herein, refers to a temperature typically in a range of from about 20° C. to about 25° C., such as (but not limited to) 21° C. to about 23° C., and including (but not limited to) about 22° C.

Any organic solvent(s) or solutions thereof known in the art or otherwise contemplated herein may be utilized in accordance with the present disclosure, so long as the photocatalysts synthesized by the methods of the present disclosure are partially or fully soluble therein. For example (but not by way of limitation), the organic solvent may comprise at least one of dichloromethane (DCM), acetone, and/or hexane.

The methods of the present disclosure may further include one or more steps that aid in increasing the yield of the photocatalyst product without requiring a chromatography step. For example (but not by way of limitation), the method may include the steps of washing the separated organic phase from step (f)(III) with an acidic solution, and then back extracting the acidic solution wash with organic solvent prior to performing the filtering step (f)(iv). In this step, the separated organic solvents from the various steps are combined prior to proceeding with the filtering step (f)(iv), and the acidic solution wash is combined with the aqueous phase for use in recovery of ligand. Any acidic solution capable of functioning in accordance with the method may be utilized; one non-limiting example thereof is an HCl solution.

Another non-limiting example of a step that may be included in the methods of the present disclosure to aid in increasing the yield of the photocatalyst product without requiring a chromatography step include the step of further extracting the aqueous phase separated in step (f)(III) with organic solvent and combining the separated, extracted organic phase with the organic phase separated in step (f)(III).

Another non-limiting example of a step that may be included in the methods of the present disclosure to aid in increasing the yield of the photocatalyst product without requiring a chromatography step include the step of (f)(VII) selectively extracting impurities from the drying reagent of (f)(VI) by washing with an organic solvent.

While the reaction mixtures removed from the reactors of the methods of the present disclosure are described as comprising a solid material and an aqueous phase, it will be understood that the reaction mixture may comprise additional components as well. For example, the reaction mixture may also potentially comprise a liquid organic phase. For example (but not by way of limitation), depending on the nature of the ligand, a liquid organic phase may be present and could actually appear as an oil floating on the aqueous phase.

EXAMPLES

Examples are provided hereinbelow. However, the present disclosure is to be understood to not be limited in its application to the specific experimentation, results, and laboratory procedures disclosed herein. Rather, the Examples are simply provided as one of various embodiments and are meant to be exemplary, not exhaustive.

According to the various Examples below, there is taught herein synthesis methods which have been utilized to obtain multi-gram quantities of multiple photocatalysts (i.e., up to at least about 2.5 g of each photocatalyst) in high purity (>99%), without the use of any chromatography column, and with the recovery of excess ligand in good yield (up to 45.7%).

All reagents utilized in the Examples were obtained from commercial suppliers (Aspira Scientific, Milpitas, Calif.; Sigma-Aldrich, St. Louis, Mo.; Oakwood Chemicals, Estill, S.C.; Alfa Aesar, Haverhill, Mass.; Strem Chemicals, Newburyport, Mass.; and VWR International, Radnor, Pa.) and used without further purification unless otherwise noted. NMR spectra were obtained on a 400 MHz Avance III spectrometer (Bruker, Billerica, Mass.) or on a 400 MHz Unity Inova spectrometer (Varian/Agilent Technologies, Santa Clara, Calif.).

Example 1

Figure 2:
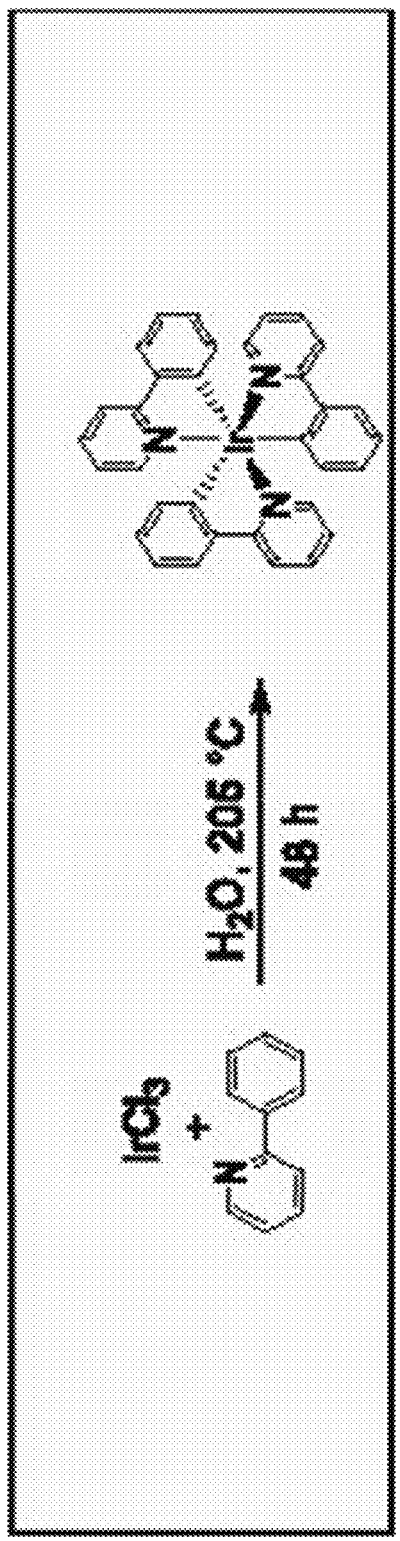
FIG. 2 illustrates one non-limiting method for synthesizing photocatalyst Fac-Tris(2-phenylpyridinato) iridium (III) as utilized in Example 1, as discussed in detail herein below.

Preparation of Fac-Tris(2-phenylpyridinato) Iridium (III) Photocatalyst (FIG. 2)

Figure 3:
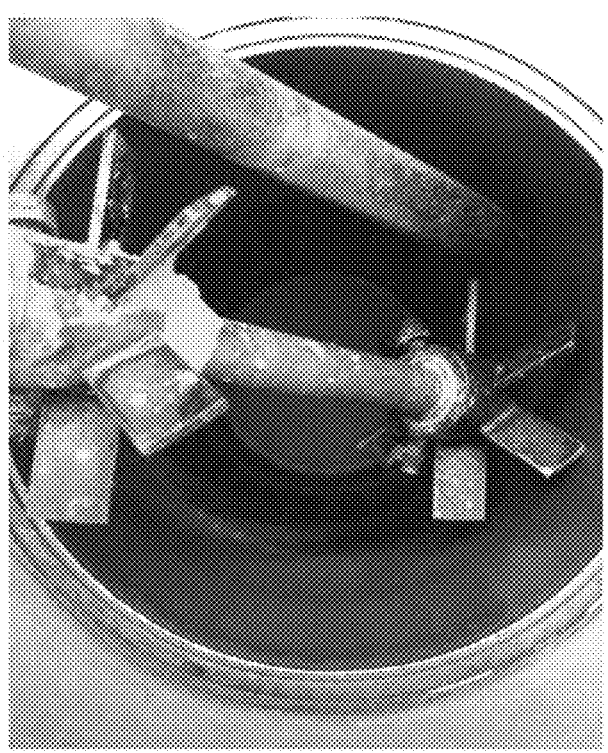
FIG. 3 photographically depicts one non-limiting example of an insoluble yellow solid photocatalyst-containing material present on internal components of a reactor after performing a synthesis as in FIG. 2.
Figure 4:
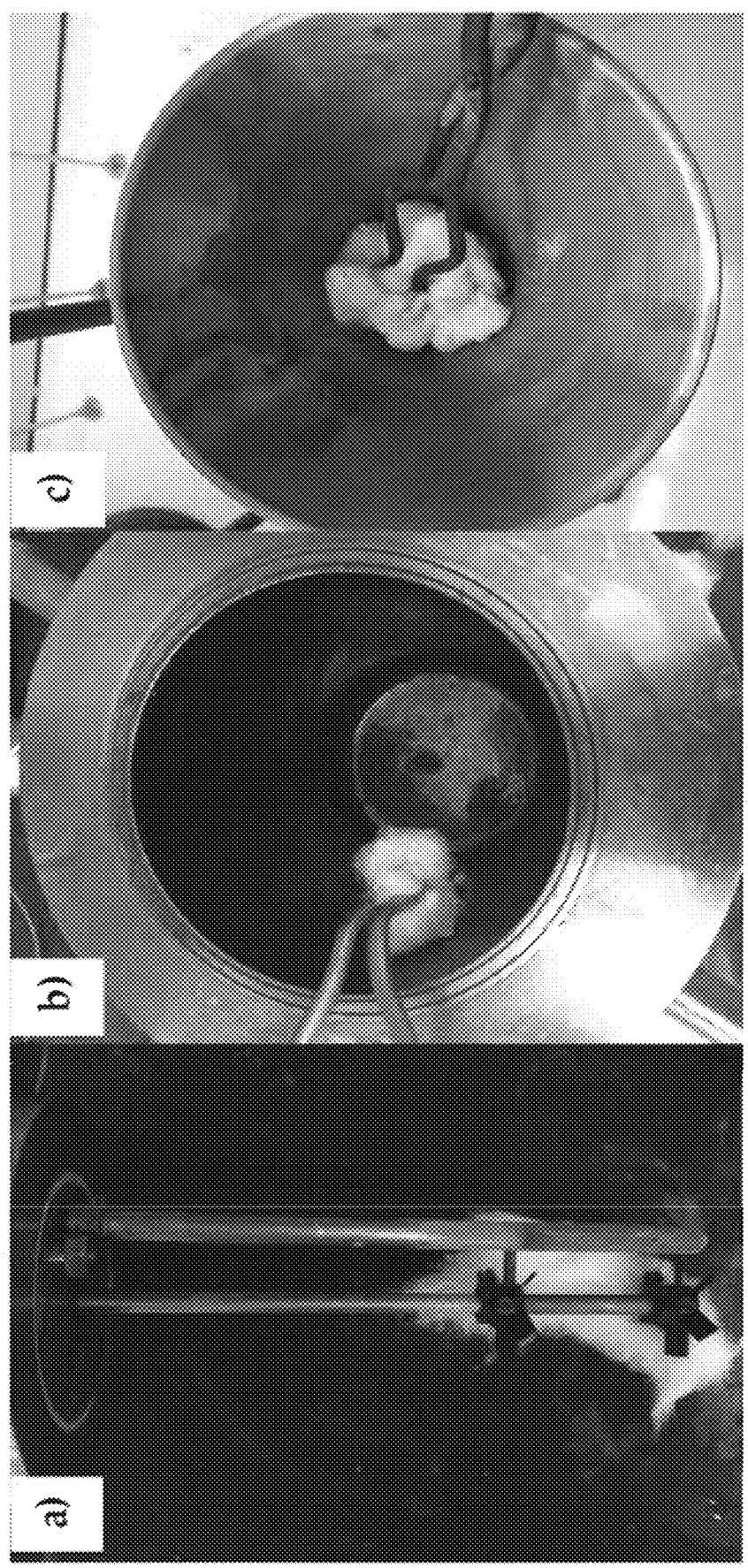
FIG. 4 graphically depicts various (but non-limiting) steps utilized in the removal of solid photocatalyst-containing material from the internal components of the reactor of FIG. 3. Panel A, yellow solid present on stirring impellers. Panel B, mechanical scraping of yellow solid off reactor walls. Panel C, extracting compound from cotton with tongs and solvent directly into reparatory funnel.

Iridium (III) chloride anhydrous (0.65 g, 2.18 mmol, 1 equivalent; Beantown Chemicals, VWR International, Radnor, Pa.), 2-phenylpyridine (3.74 mL, 26.1 mmol, 12.0 equivalents; AK Scientific, Union City, Calif.), and 0.65 L of deionized (DI) water (0.003 M with respect to $IrCl_3$) was added to a 1 L Parr reactor. The reaction mixture was pressurized with argon (10.0 psi), stirred, and then depressurized three times, and finally charged again with argon before sealing. The reaction mixture was heated to 205° C. for 48 h. Then the reactor was cooled to 20° C. with internal cooling coils. At the end of the experiment, the reactor was left in the stand, and the contents were cooled to 20° C. using cold water. After cooling, the reactor was opened, revealing an insoluble yellow solid on the surfaces (FIG. 3 and Panel (a) of FIG. 4) and dispersed in the aqueous phase. All contents were transferred slowly to a 6 L separatory funnel aided by a large 5 cm glass funnel. Then the interior of the reactor was mechanically scraped (to extract the yellow material) with metal tongs, cotton balls (25 in total), and 500 mL of dichloromethane (DCM) from a spray bottle (Panel (b) of FIG. 4), and again all contents were added to the separatory funnel. While still in the funnel, the cotton was rinsed with 25 mL of DCM from a spray bottle and evenly pressed with tongs to release the yellow material from the cotton (Panel (c) of FIG. 4). After removing the cotton, the solution was then diluted with 2.5 L of DCM.

The cotton was placed directly into the separatory funnel solely to cut process time. It will be understood that one alternative to this method is to place the cotton into a beaker and then extract the cotton material with DCM. The DCM extracts can then be added to the separatory funnel.

The separatory funnel was shaken vigorously, allowed to settle and again shaken, and the organic layer was then slowly separated from the aqueous layer; the aqueous layer was then further extracted with more DCM (3×10 mL), and the organic layers were combined. The aqueous layers were kept for future ligand recovery.

The combined organic layers were washed with a 1 M HCl solution, with vigorous mixing prior to separation (3×900 mL). Each HCl wash was then back extracted with DCM (3×10 mL) to insure complete recovery of the product. After the final wash, the organic layer was filtered slowly (20 min) through a CELITE® (35 g) pad (Imerys Minerals California, Inc., San Jose, Calif.) on top of a 150 mL medium porosity sintered glass funnel, into a 3 L roundbottomed flask, and then dried with 30 g of $MgSO_4$. After filtering the drying reagent using a 4 L Erlenmeyer flask fitted with a 5 cm funnel/cotton plug, a homogenous aliquot was removed for NMR analysis. Finally, the solvent was removed in batches by transferring to a 2.5 L roundbottomed flask by rotary evaporation (35° C., 30 mm Hg, 150 rpm) to afford 1.35 g (94%) of Ir(ppy)$_3$ as a bright yellow solid.

While not required by the present disclosure, further purification of Ir(ppy)$_3$ can be performed by adding the yellow solid to a 1 L round-bottomed flask and adding 600 mL of distilled hexanes. The solid material was then sonicated until a uniform slurry was achieved, and 5 mL of dichloromethane was added. The liquid was swirled, giving a slight yellow tint to the solution and thus indicating successful dissolution of a colored compound and selective extraction of the impurities. Then the slurry was slowly poured through a 50 mL fine porosity sintered glass funnel to collect the yellow solid, and the filtrate was collected into a 1 L Erlenmeyer flask. The yellow solid was air dried on the filter to afford 1.29 g, 91% yield of the product in >97% purity.

Figure 5:
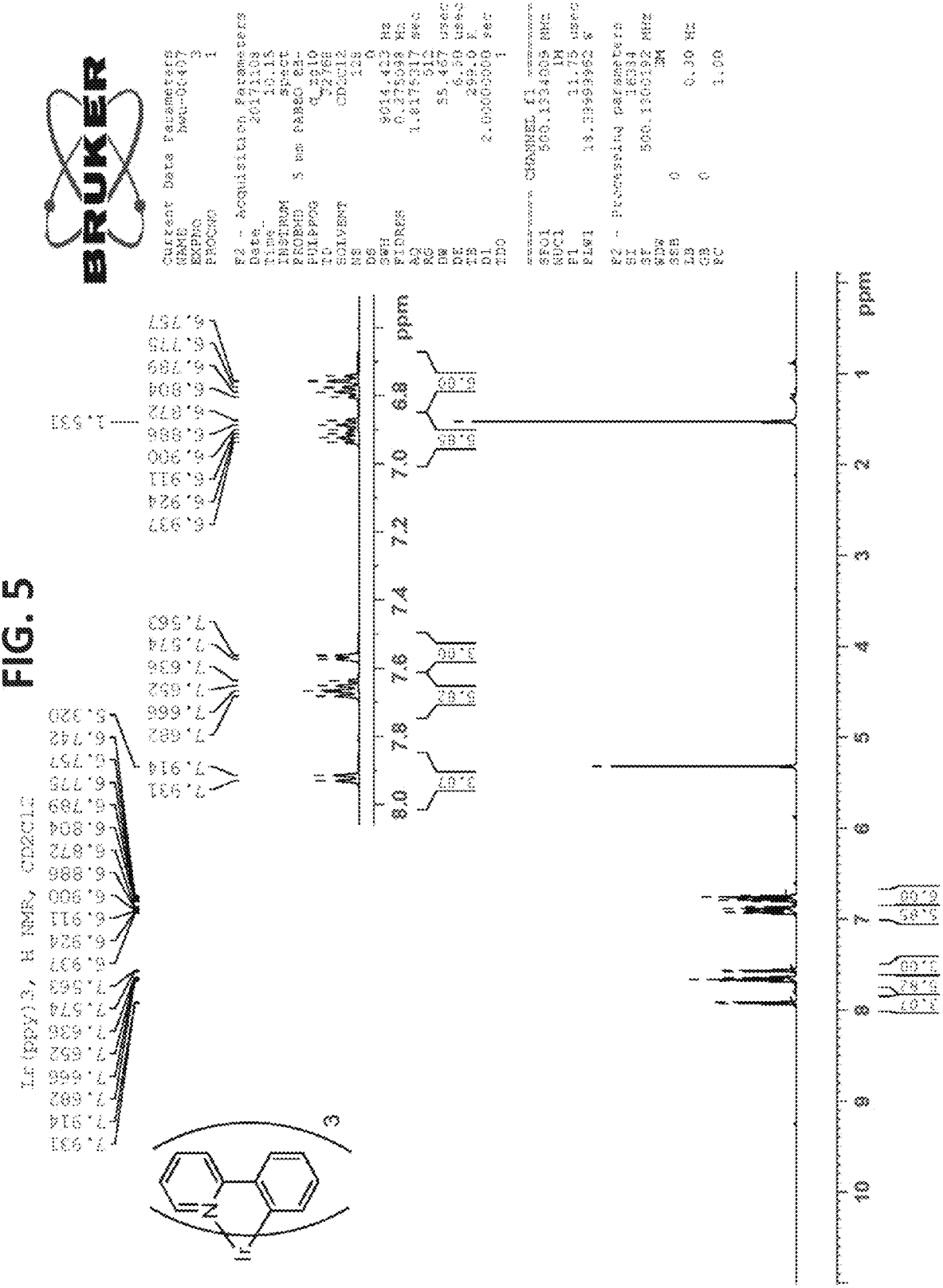
FIG. 5 contains $^1H$ NMR spectra of Fac-Tris(2-phenylpyridinato) iridium (III), as produced in Example 1.

Characterization of fac-tris(2-phenylpyridinato) iridium (III): FIG. 5—$^1$H NMR (500 MHz, CD$_2$Cl$_2$) (5.32 ppm for CH$_2$Cl$_2$ in CD$_2$Cl$_2$) δ: 6.78 (dt, J=16.1, 7.4 Hz, 6H), 6.90 (dt, J=18.9, 6.4 Hz, 6H), 7.57 (d, J=5.3 Hz, 3H), 7.64-7.68 (m, 6H), 7.92 (d, J=8.2 Hz, 3H).

Figure 6:
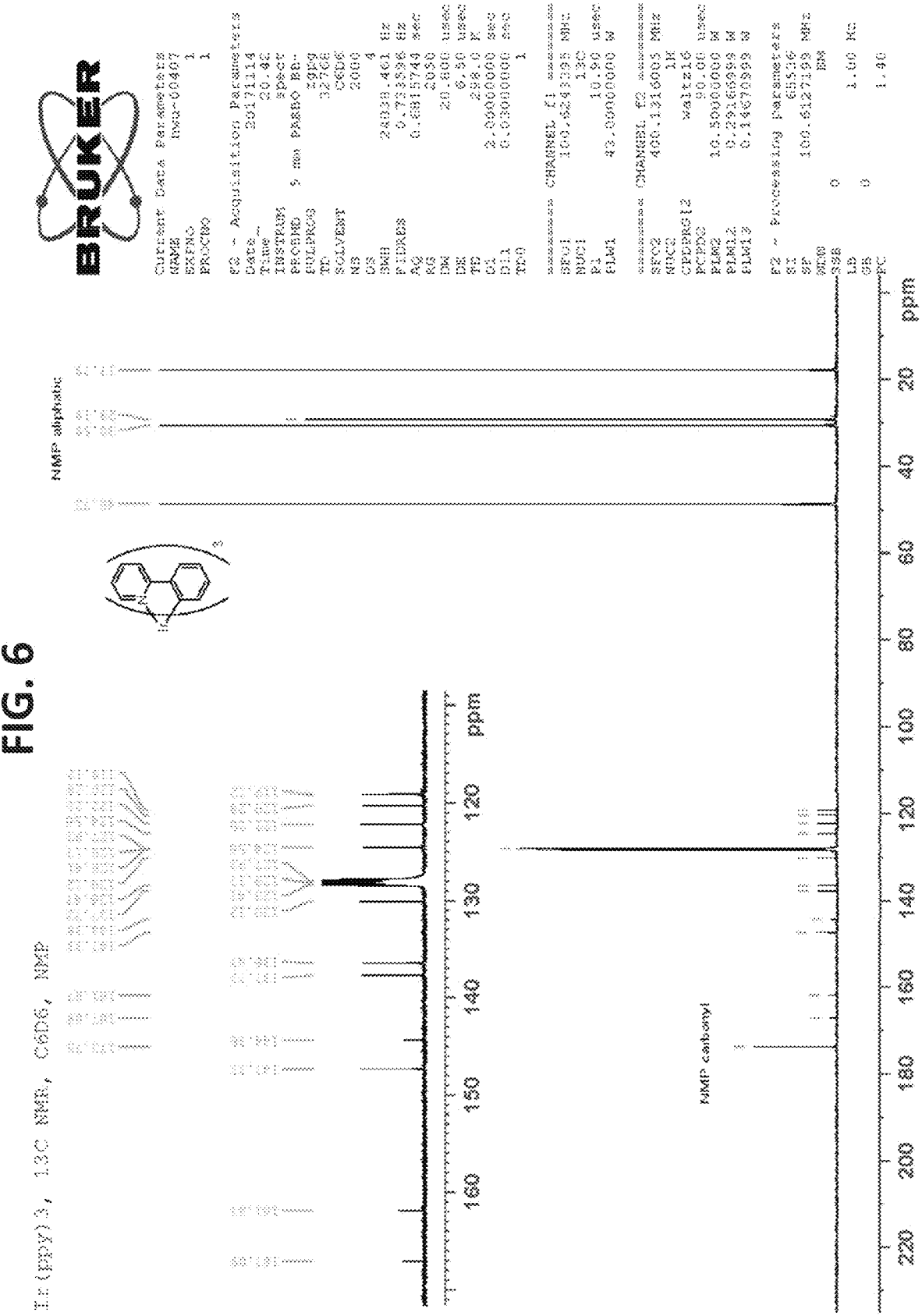
FIG. 6 contains $^{13}C$ NMR spectra of Fac-Tris(2-phenylpyridinato) iridium (III), as produced in Example 1.

FIG. 6—$^{13}$C NMR (400 MHz, C$_6$D$_6$ with NMP) δ: 119.1, 120.3, 122.2, 124.6, 130.1, 136.5, 137.7, 144.4, 147.3, 161.9, 167.1. IR (film): 3034, 2923, 1599, 1580, 1560, 1470, 1413, 1261, 1159, 752, 732 cm$^{-1}$.

Figure 7:
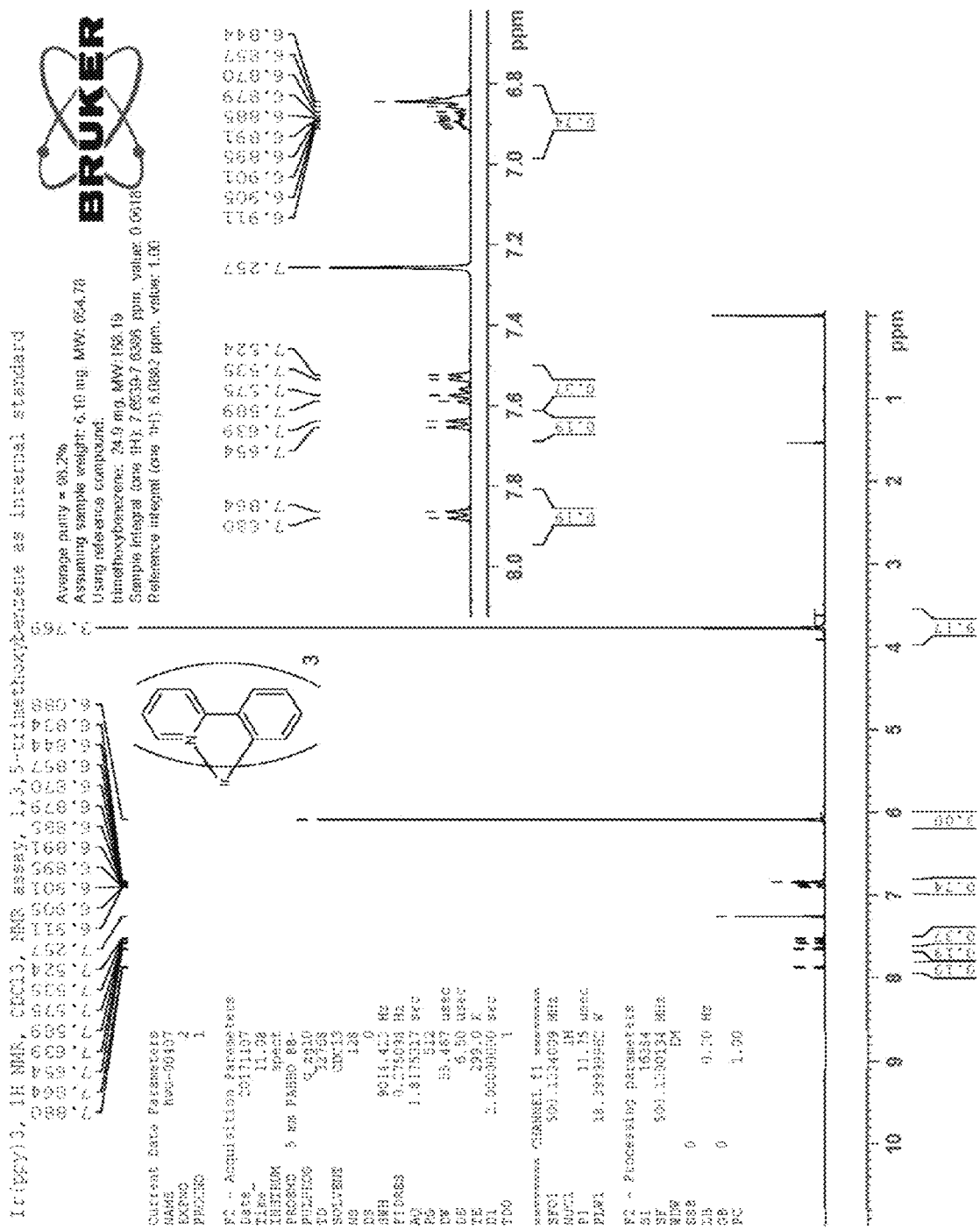
FIG. 7 contains $^1H$ NMR spectra of Fac-Tris(2-phenylpyridinato) iridium (III), as produced in Example 1, with 1,3,5-trimethoxybenzene as internal standard.

A second reaction on the same scale provided 1.30 g (91%) of the product in >98% purity (FIG. 7).

The weight percent was determined by quantitative NMR pdf using trimethoxybenzene as the internal standard. The solubility of Ir(ppy)$_3$ in most deuterated solvents is low, which makes weighing out the necessarily small amounts of dissolvable compound challenging. It is best to accurately weigh out a larger sample (>100 mg of the standard or compound) and dissolve the compound into protio-dichloromethane using a volumetric flask to give an accurate molar solution. Then appropriate volumes of the standard and compound solutions can be mixed. Next, the protio-solvent was removed and the mixture redissolved in the appropriate deuterated solvent. A proton NMR spectrum was thus obtained for the mixture with a minimum relaxation delay of 30 s.

If using more expensive ligands, it may be economical to recover the valuable ligand. Below is an example of recovery of the 2-phenylpyridine ligand. The previously retained acidic aqueous layers from a 4.46 mmol reaction were added to a 4 L Erlenmeyer flask with a 60 mm PTFE octagon stir bar. The solution was stirred and slowly brought to pH 10 by adding 119 g of NaOH pellets in 10 portions. The solution was added to a 6 L reparatory funnel, and the ligand was extracted from the salty water with DCM (6×1.2 L). The combined organic extracts were added to a 20 L metal canister and were dried with 20 g of MgSO$_4$. After filtering the drying reagent through a 5 cm funnel with a cotton plug into another 20 L canister, the solvent was removed in batches by utilizing a continuous rotary evaporation setup (35° C., 130 mm Hg, 100 rpm) to afford 5.90 g (96.4%) (based on excess 9 equiv) of 2-phenylpyridine was recovered in 97.7-98.5% purity, as determined by quantitative $^1$H NMR using 1,3,5-trimethoxybenzene as the internal standard.

Discussion of Example 1

The three main objectives of synthesis and isolation methods of this Example were to maintain high purity of complex on a gram scale, eliminate chromatography, and recover the excess ligand. This method has been utilized to obtain multigram quantities of the photocatalyst (up to 2.85 g) in high purity (>97%), without the use of a column, and with excellent recovery of excess ligand in good yield (up to 97.0%). Similar results were also obtained in the methods described in Examples below, indicating that the method works with more elaborate ligands that are less accessible.

Additionally, it is also possible to recover the organic solvent utilized in this method in high purity.

The methods disclosed herein are applicable to all members of this family of photocatalysts. Consequently, this method will facilitate exploration of the chemistry of these Ir-complexes, as well as enable applications which may require more substantial quantities of Ir-photocatalysts.

Example 2

Figure 9:
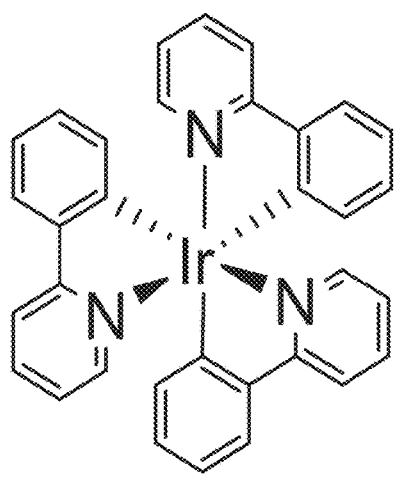
FIG. 9 illustrates the structure of photocatalyst Fac-Tris (2-phenylpyridinato) iridium (III), as produced in Examples 1-3.

Synthesis of Fac-Tris(2-phenylpyridinato) Iridium (III) Photocatalyst (FIG. 9)

A Parr reactor (1.5 L) was charged with 1.3 g iridium (III) chloride trihydrate (1 equivalent), 8.1 g of 2-phenylpyridine (12 equivalents), and 1.3 L of deionized (DI) water (0.003 M). The reaction mixture was pressurized with Argon gas (Ar; 30 psi) and depressurized three times, then finally charged again with Ar before sealing. The reaction mixture was heated at 200° C. for 48 h. After cooling to room temperature, the reaction mixture was extracted with dichloromethane (DCM; 3×300 mL), completely cleaned with DCM/cotton, and washed with water (2×200 mL). The organic layer was then washed with a 1 M HCl solution (4×100 mL). The combined organic portion was filtered through a CELITE® pad (Imerys Minerals California, Inc., San Jose, Calif.) on top of a coarse fritted filter (4 cm in height), and dried with MgSO$_4$. After filtering the drying reagent, a homogenous aliquot was removed for analysis. Finally, the solvent was removed via a rotary evaporator (rotovap) to obtain the photocatalyst Ir(ppy)$_3$ (illustrated in FIG. 9) in 2.25 g, 79% yield in >99% purity, as compared to integrations of satellite signals of the signal in the $^1$H NMR.

Ligand recovery: The aqueous water layers were brought to pH 10 with 50 g of NaOH pellets, and the ligand was extracted from the water with DCM×6. The combined organic solution was dried with MgSO$_4$, and the solvent was removed via a rotovap to obtain 4.55 g, 75% yield (based on excess of ligand) was recovered.

Continuing with the present example and providing further details:

Fac-Tris(2-phenylpyridinato) iridium (III) (A). Iridium (III) chloride trihydrate (1.30 g, 4.35 mmol, 1 equivalent), 2-phenylpyridine (7.46 mL, 52.2 mmol, 12 equivalent), and 1.3 L of DI water (0.003 M with respect to IrCl$_3$) were added to a 1.5 L Parr reactor. The reaction mixture was then pressurized with Argon (10.0 psi), shaken, and then depressurized three times, and finally charged again with Argon before sealing. The reaction mixture was heated to 200° C. for 48.0 h. Then the reactor was cooled to room temperature, and the reactor was opened, revealing an insoluble yellow solid on the surfaces and dispersed in the aqueous phase. All contents were transferred slowly to a 6 L reparatory funnel with a large 5 cm glass funnel. The Parr reactor was extracted with cotton balls (6 in total) and 1.5 mL of DCM in 6 portions, and again all contents were added to the funnel. The cotton, while in the funnel, was pressed to extract all solvent from the cotton material. The organic layer was then separated from the aqueous layer, and the aqueous layer was rinsed with 10 mL of DCM. All aqueous layers were kept for ligand recovery. The combined organic layer was washed with a 1 M HCl solution (3×900 mL). The combined organic portions were filtered through a CELITE® (40.0 g) pad (Imerys Minerals California, Inc., San Jose, Calif.) on top of a 250 mL, medium porosity, sintered glass funnel into a 4 L Erlenmeyer flask and dried with 10 g of $MgSO_4$. After filtering the drying reagent through a 150 mm funnel with cotton plug, a homogenous aliquot was removed for NMR analysis. Finally, the solvent was removed by rotary evaporation (35° C., 30 mmHg) to afford $Ir(ppy)_3$ as a bright yellow solid in 97.7% yield (2.78 g) in >97% purity, as compared to integrations of satellite signals of the signal in the $^1H$ NMR.

Further purification of $Ir(ppy)_3$ can be performed by adding 2.783 g of the yellow solid to a round-bottom flask and adding 500 mL of distilled hexanes. The solid material was sonicated until a uniform slurry was achieved, and 6 mL of dichloromethane was added. The liquid phase had a slight yellow tint, indicating successful dissolution of a colored compound and selective extraction of the impurities. Then the slurry was poured into a 150 mL fine porosity sintered glass funnel and collected into a 1 L Erlenmeyer flask to catch the $Ir(ppy)_3$ solid. The solid was left on the filter to air dry to afford 91% yield (2.53 g) in >99% purity, as compared to integrations of satellite signals of the signal in the $^1H$ NMR.

Example 3

Figure 8:
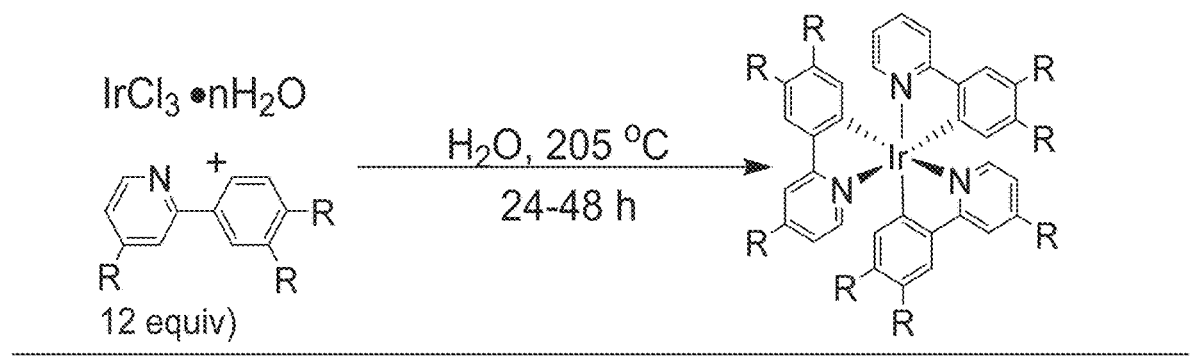
FIG. 8 illustrates another non-limiting method for synthesizing photocatalyst Fac-Tris(2-phenylpyridinato) iridium (III) as utilized in Example 3.

Synthesis of Fac-Tris(2-phenylpyridinato) Iridium (III) Photocatalyst (FIGS. 8-9)

Iridium (III) chloride anhydrous (1.30 g, 4.36 mmol, 1 equiv), 2-phenylpyridine (7.47 mL, 52.2 mmol, 12.0 equiv), and 1.30 L of DI water (0.003 M with respect to $IrCl_3$) were added to a 2 L Parr reactor. The reaction mixture was then pressurized with Argon (10.0 PSI), stirred, and then depressurized three times, and finally charged again with Argon before sealing. The reaction mixture was heated to 205° C. for 48.0 h. Then the reactor was cooled to room temperature with an ice bath, and the reactor was opened after cooling, revealing an insoluble yellow solid on the surfaces and dispersed in the aqueous phase. All contents were transferred slowly to a 6 L separatory funnel aided by a large 5 cm glass funnel. Then the interior of the reactor was mechanically scraped (to extract the yellow material) with metal tongs, cotton balls (25 in total), and 500 mL of DCM from a spray bottle, and again all contents were added to the separatory funnel. While still in the funnel, the cotton was rinsed with 25 mL of DCM from a spray bottle and evenly pressed with tongs to release the yellow material from the cotton. After removing the cotton, the solution was then diluted with 2.5 L of DCM. The separatory funnel was shaken vigorously, allowed to settle and again shaken, and the organic layer was then slowly separated from the aqueous layer; the aqueous layer was further extracted with more DCM (3×10 mL), and the organic layers were combined. The aqueous layers were kept for future ligand recovery. The combined organic layer was washed with a 1 M HCl solution, with vigorous mixing prior to separation (3×900 mL). Each HCl wash was then back extracted with DCM (3×10 mL) to insure complete recovery of the product. After the final wash, the organic layer was filtered slowly (20 min) through a CELITE® (35 g) pad (Imerys Minerals California, Inc., San Jose, Calif.) on top of a 150 mL medium porosity sintered glass funnel, into a 3 L round bottom flask, and then dried with 30 g of $MgSO_4$. After filtering the drying reagent using a 4 L Erlenmeyer flask fitted with a 5 cm funnel/cotton plug, a homogenous aliquot was removed for NMR analysis. Finally, the solvent was removed in batches by transferring to a 2.5 L round bottom flask by rotary evaporation (35° C., 30 mm Hg, 150 rpm) to afford $Ir(ppy)_3$ as a bright yellow solid in 97.5-99.1% yield (2.78 g) in 96.3%-97.5% purity as compared to a standard signal (trimethoxybenzene) in the $^1H$ NMR (FIG. 10).

Further purification of $Ir(ppy)_3$ can be performed by adding 2.78 g of the yellow solid to a 1 L round-bottom flask and adding 600 mL of distilled hexanes. The solid material was then sonicated until a uniform slurry was achieved, and 5 mL of dichloromethane was added. The liquid was swirled, giving a slight yellow tint to the solution, indicating successful dissolution of a colored compound and selective extraction of the impurities. Then the slurry was slowly poured through a 50 mL fine porosity sintered glass funnel to catch the $Ir(ppy)_3$ solid, and the filtrate was collected into a 1 L Erlenmeyer flask. The yellow solid was left on the filter to air dry to afford 91.6-93.0% yield (2.61 g) in 97.8%-99.1% purity, compared to integrations of a standard signal (trimethoxybenzene) in the $^1H$ NMR.

Figure 10:
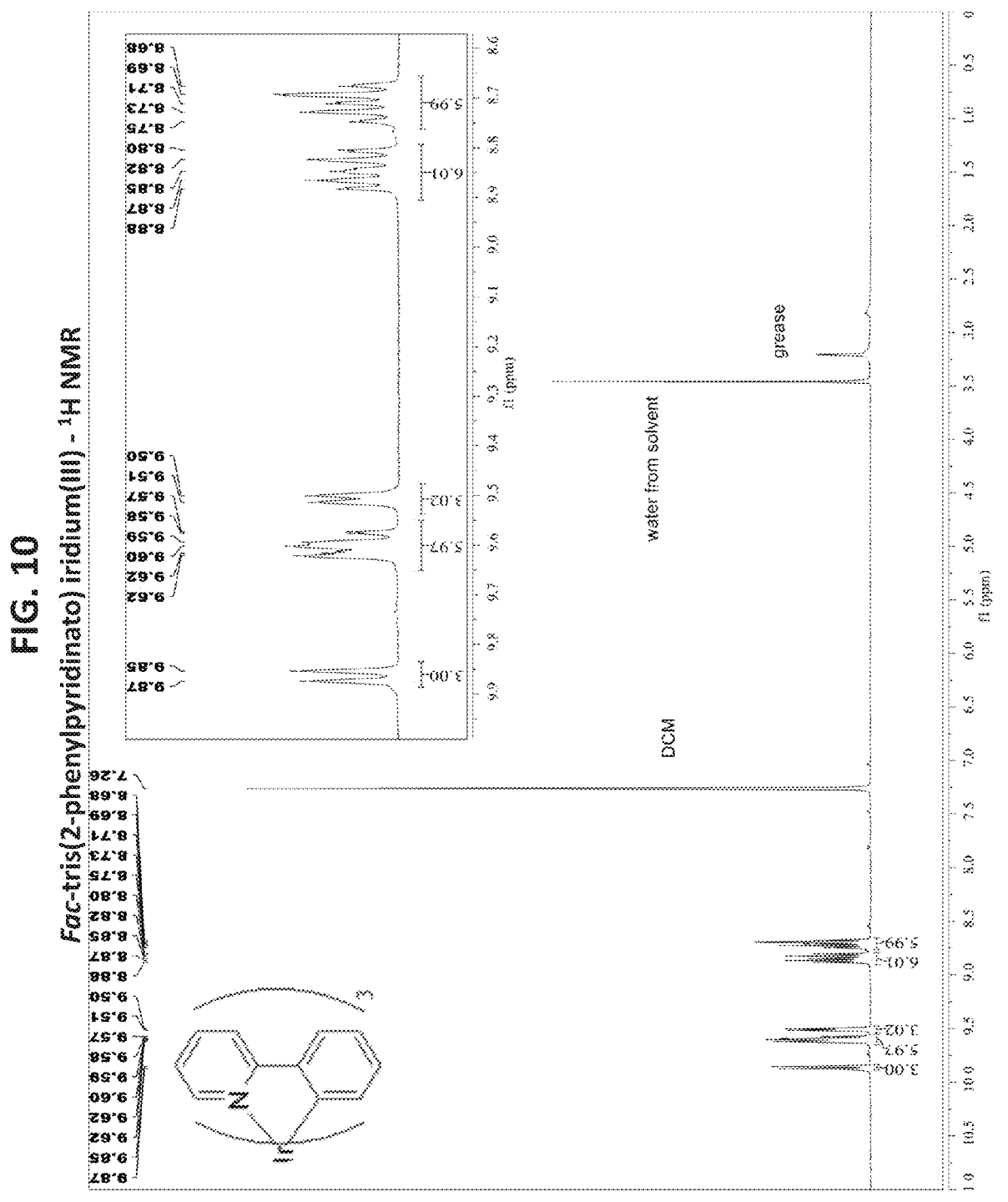

FIG. 10 $^1H$ NMR (400 MHz, Methylene Chloride-d2) δ 9.86 (d, J=8.2 Hz, 1H), 9.60 (td, J=8.1, 1.8 Hz, 2H), 9.51 (d, J=5.5 Hz, 1H), 8.93-8.77 (m, 1H), 8.71 (dt, J=14.1, 7.0 Hz, 1H).

Figure 11:
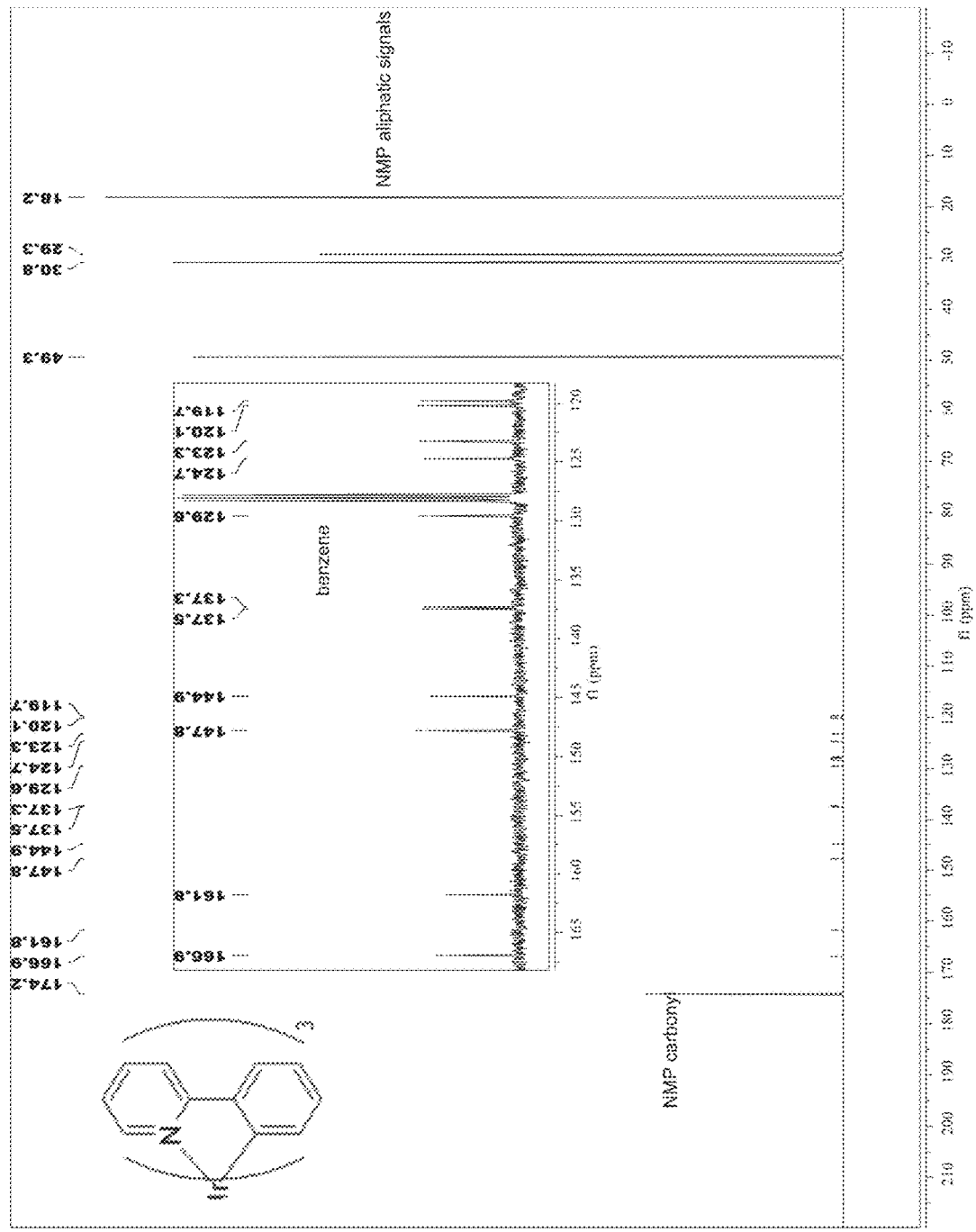
FIG. 11 contains $^{13}C$ NMR spectra of Fac-Tris(2-phenylpyridinato) iridium(III), as produced in Example 3.

FIG. 11—$^{13}C$ NMR (101 MHz, $C_6D_6$/NMP) δ 166.9, 161.8, 147.8, 144.9, 137.5, 137.3, 129.6, 124.7, 123.3, 120.1, 119.7. FT-IR (neat) cm-1 3035, 1560, 1260, 749.

Recovery of 2-phenylpyridine ligand: The previously retained aqueous layers were added to a 4 L Erlenmeyer flask with a 60 mm PTFE octagon stir bar. The solution was stirred and slowly brought to pH 10 by adding 119 g of NaOH pellets in 10 portions. The solution was added to a 6 L reparatory funnel, and the ligand was extracted from the salty water with DCM (6×1.2 L). The combined organic extracts were added to a 20 L metal canister and were dried with 20 g of $MgSO_4$. After filtering the drying reagent through a 5 cm funnel with a cotton plug into another 20 L canister, the solvent was removed in batches by utilizing a continuous rotary evaporation setup (35° C., 130 mm Hg, 100 rpm) to afford 5.90 g, 96.4-97.0% (based on excess 9 equiv) of 2-phenylpyridine was recovered in 97.7-98.5% purity, compared to a standard signal (trimethoxybenzene) in the $^1H$ NMR.

Figure 12:
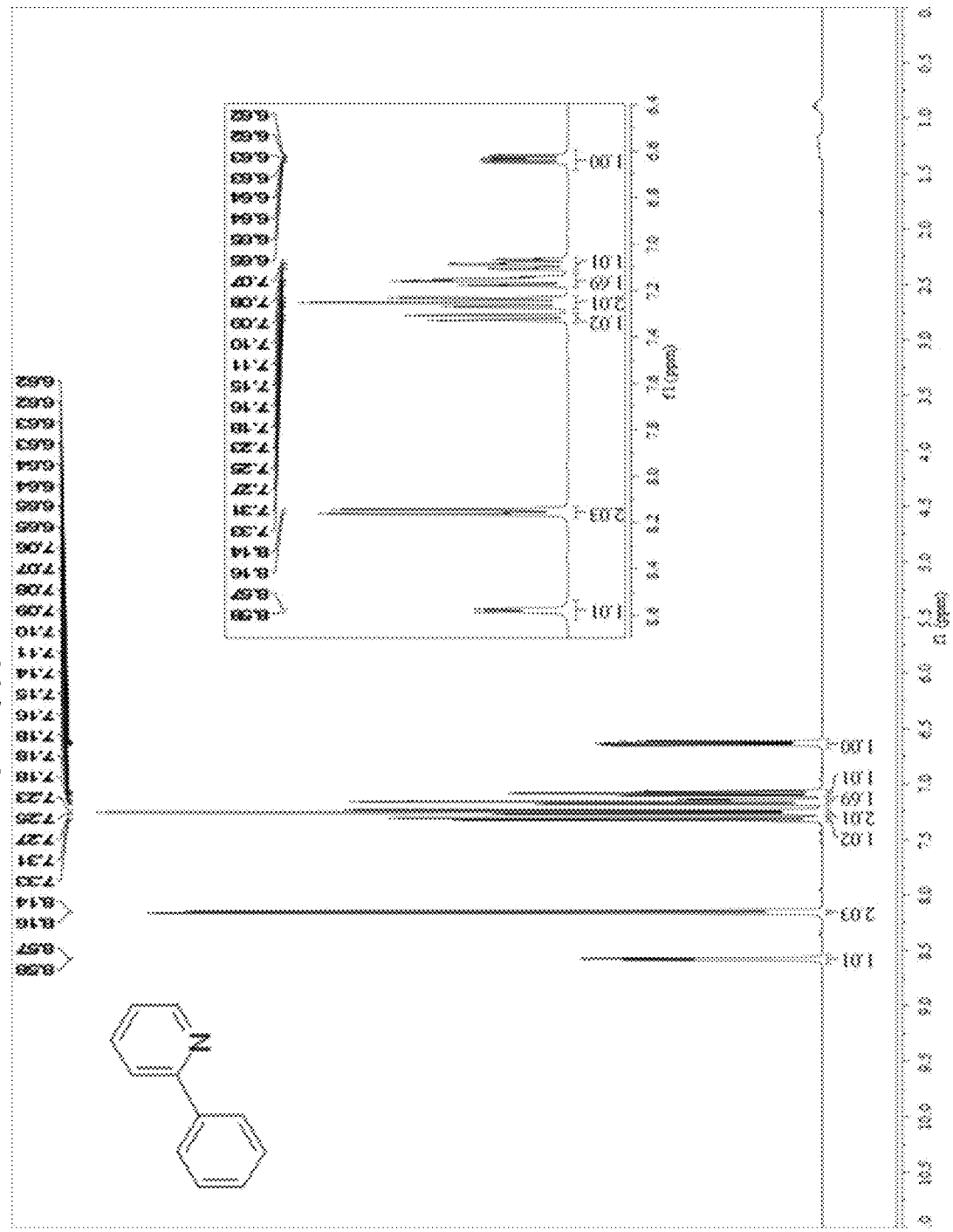
FIG. 12 contains $^1H$ NMR spectra of ligand 2-phenylpyridine, as recovered in Example 3.

FIG. 12—$^1H$ NMR (400 MHz, Benzene-d6) δ 8.58 (d, J=4.7 Hz, 1H), 8.15 (d, J=7.2 Hz, 1H), 7.32 (d, J=8.0 Hz, 1H), 7.25 (t, J=7.5 Hz, 1H), 7.19-7.12 (m, 2H), 7.09 (td, J=7.7, 1.9 Hz, 1H), 6.63 (ddd, J=7.4, 4.8, 1.0 Hz, 1H).

Figure 13:
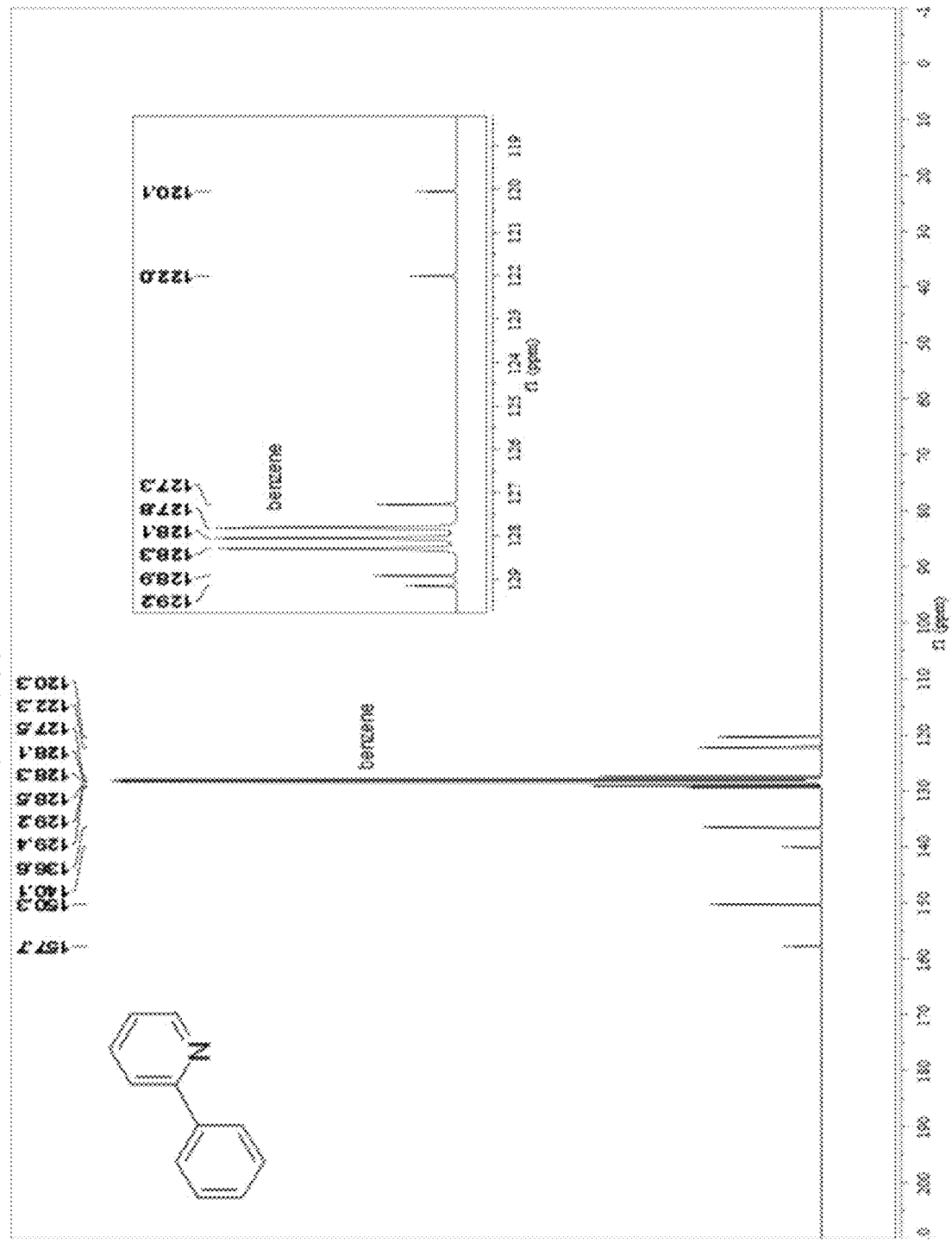
FIG. 13 contains $^{13}C$ NMR spectra of ligand 2-phenylpyridine, as recovered in Example 3.

FIG. 13—$^{13}C$ NMR (101 MHz, $C_6D_6$) δ 157.7, 150.3, 140.1, 136.6, 129.4, 129.2, 127.5, 122.3, 120.3. FT-IR (neat) cm-1 3061, 1579, 1293, 743.

Example 4

Figure 14:
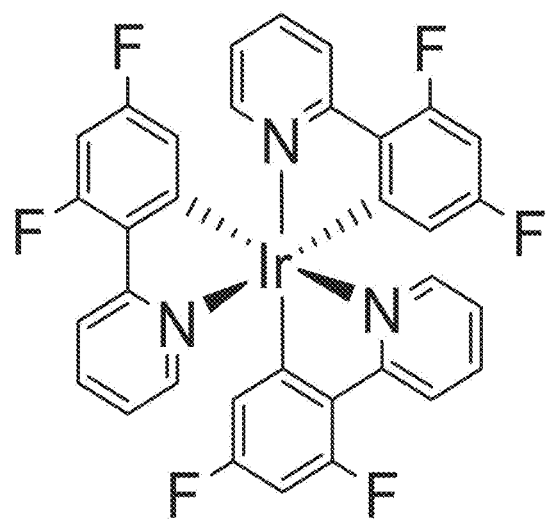
FIG. 14 illustrates the structure of photocatalyst Fac-Tris (2-(4,6-difluorophenyl)pyridinato) iridium (III), as produced in Examples 4-5.

Synthesis of Fac-Tris(2-(4,6-difluorophenyl)pyridinato) Iridium (III) Photocatalyst (FIG. 14)

A Parr reactor (1.5 L) was charged with 1.1 g iridium (III) chloride trihydrate (1 equivalent), 8.4 g of 2-(2,4-difluorophenyl)pyridine (12 equivalents), and 1.1 L of DI water (0.003 M). The reaction mixture was pressurized (30 psi) and depressurized with Ar three times, then finally charged again with Ar before sealing. The reaction mixture was heated at 200° C. for 48 h. After cooling the reactor to room temperature, the reaction mixture was extracted with DCM (3×300 mL), completely cleaned with DCM/cotton, and washed with water (2×200 mL). The organic layer was then washed with a 1 M HCl solution (4×100 ml). The combined organic portion was filtered through a CELITE® pad (Imerys Minerals California, Inc., San Jose, Calif.) and dried with MgSO$_4$. At this point, a homogenous aliquot was removed for analysis. Finally, the solvent was removed via a rotovap to obtain Ir(dFppy)$_3$ (as illustrated in FIG. 14) in 2.01 g, 72% yield in >99% purity, as compared to integrations of sidebands of some signal in the $^1$H NMR.

Ligand recovery: The aqueous water layers were brought to pH 10 with 3 M NaOH solution, and the ligand was extracted from the water with DCM×4. The solution was dried with MgSO$_4$, and the solvent was removed via a rotovap to obtain 2.89 g; 45.7% yield (based on excess) of ligand was recovered.

Continuing with the present example and providing further details:

Synthesis of Fac-Tris(2-(4,6-difluorophenyl)pyridinato) iridium (III) (A). Iridium (III) chloride trihydrate (1.00 g, 3.35 mmol, 1 equivalent), 2-(4,6-difluorophenylpyridine (7.68 g, 40.2 mmol, 12 equivalents), and 1.0 L of DI water (0.003 M with respect to IrCl$_3$) were added to a 1.5 L Parr reactor. The reaction mixture was then pressurized with Argon (10.0 psi), shaken, and then depressurized three times, and finally charged again with Argon before sealing. The reaction mixture was heated to 200° C. for 48.0 h. Then the reactor was cooled to room temperature and opened, revealing an insoluble yellow solid on the surfaces and dispersed in the aqueous phase. All contents were transferred slowly to a 6 L reparatory funnel with a large 5 cm glass funnel. The Parr reactor was extracted with cotton balls (6 in total) and 1.8 L of DCM in 6 portions, and again all contents were added to the funnel. While in the funnel, the cotton was pressed to extract all solvent from the cotton material. The organic layer was then separated from the aqueous layer, and the aqueous layer was rinsed with 10 mL of DCM. All aqueous layers were kept for ligand recovery. The combined organic layer was washed with a 1 M HCl solution (3×1200 mL). The combined organic portions were filtered through a CELITE® (40.0 g) pad (Imerys Minerals California, Inc., San Jose, Calif.) on top of a 250 mL, medium porosity, sintered glass funnel into a 4 L Erlenmeyer flask and dried with 10 g of MgSO$_4$. After filtering the drying reagent through a 15 cm funnel with cotton plug, a homogenous aliquot was removed for NMR analysis. Finally, the solvent was removed by rotary evaporation (35° C., 30 mmHg) to afford Ir(diFppy)$_3$ as a bright yellow solid in 85.1% yield (2.170 g) in >95% purity, as compared to integrations of satellite signals of the signal in the $^1$H NMR.

Further purification of Ir(diFppy)$_3$ can be performed by adding 2.170 g of the yellow solid to a round-bottom flask and adding 500 mL of distilled hexanes. The solid material was sonicated until a uniform slurry was achieved, and 6 mL of dichloromethane was added. The liquid phase had a slight yellow tint, indicating successful dissolution of a colored compound and selective extraction of the impurities. Then the slurry was poured into a 150 mL fine porosity sintered glass funnel and collected into a 1 L Erlenmeyer flask to catch the Ir(diFppy)$_3$ solid. The solid was left on the filter to air dry to afford 80% yield (2.04 g) in >99% purity, as compared to integrations of satellite signals of the signal in the $^1$H NMR.

Ligand recovery: The aqueous water layers were brought to pH 10 with 60 g of NaOH pellets, and the ligand was extracted from the water with DCM×6. The solution was dried with MgSO$_4$, and the solvent was removed via a rotovap to obtain 2.59 g, 45% yield (based on excess of ligand) was recovered.

Note: The solubility of these photocatalysts in relation to impurities in these particular examples is significantly low. A homogenous aliquot insures that NMR molar ratios are accurate. Trituration of solid material can be employed to obtain high purity using THF/H$_2$O or MeOH/H$_2$O combinations. By dissolving catalyst in a minimum amount of organic solvent in a test tube, one would slowly add water until solid crashes out of solution. Then the solution is centrifuged down, and the solid is collected by filtration and dried under high vacuum. In addition, the impurities can be selectively dissolved in a hexane/DCM solution by dissolving catalyst in hexanes and adding DCM dropwise until the yellow color of the solution appears. Then the supernatant is decanted off, and the solid is dried under high vacuum.

Example 5

Synthesis of Fac-Tris(2-(4,6-difluorophenyl)pyridinato) Iridium (III) Photocatalyst (FIG. 14)

Iridium (III) chloride anhydrous (1.00 g, 3.35 mmol, 1 equiv), 2-(4,6-difluoro)phenylpyridine (6.13 mL, 40.2 mmol, 12 equiv), and 1.00 L of DI water (0.003 M with respect to IrCl$_3$) were added to a 2 L Parr reactor. The reaction mixture was then pressurized with Argon (10.0 PSI), stirred, and then depressurized three times and finally charged again with argon before sealing. The reaction mixture was heated to 205° C. for 48.0 h. Then the reactor was cooled to room temperature with an ice bath, and the reactor was opened after cooling, revealing an insoluble yellow solid on the surfaces and dispersed in the aqueous phase. All contents were transferred slowly to a 6 L separatory funnel aided by a large 5 cm glass funnel. Then the interior of the reactor was mechanically scraped (to extract the yellow material) with metal tongs, cotton balls (25 in total), and 500 mL of DCM from a 500 mL spray bottle, and again all contents were added to the separatory funnel. While still in the funnel, the cotton was rinsed with 25 mL of DCM from a spray bottle and evenly pressed with tongs to release the yellow material from the cotton. After removing the cotton, the solution was then diluted with 2.5 L of DCM. The separatory funnel was shaken vigorously, allowed to settle and again shaken, and the organic layer was then slowly separated from the aqueous layer; the aqueous layer was further extracted with DCM (3×10 mL), and the organic layers were combined. The aqueous layers were kept for future ligand recovery. The combined organic layer was washed with a 1 M HCl solution with vigorous mixing (4×1 L). Each HCl wash was back extracted with DCM (3×10 mL) to insure complete recovery of the product. After the final wash, the organic layer was filtered slowly (20 min) through a CELITE® (35 g) pad (Imerys Minerals California, Inc., San Jose, Calif.) on top of a 150 mL medium porosity sintered glass funnel into a 3 L round bottom flask, and dried with 50 g of MgSO$_4$. The drying reagent was filtered using a 4 L Erlenmeyer flask fitted with a 5 cm funnel/cotton plug. At this point, a homogenous aliquot was removed for NMR analysis. Finally, the solvent was removed in batches by transferring to a 2.5 L round bottom flask by rotary evaporation (35° C., 30 mm Hg, 150 rpm) to afford Ir(diFppy)$_3$ as a yellow solid in 90.9% yield (2.32 g) in 90.8% purity compared to a standard signal in the $^{19}$F NMR.

Further purification of Ir(diFppy)$_3$ can be performed by adding 2.32 g of the yellow solid to a 1 L round-bottom flask and adding 600 mL of distilled hexanes. The solid material was sonicated until a uniform slurry was achieved, and 5 mL of dichloromethane was added. The liquid was swirled, giving a slight yellow tint to the solution and indicating successful dissolution of a colored compound and selective extraction of the impurities. Then the product slurry was slowly filtered through a 50 mL fine porosity sintered glass funnel, and the filtrate was collected into a 1 L Erlenmeyer flask. The yellow solid was left on the filter to air dry to afford 71.4% yield (1.82 g) in 97.2% purity, compared to integrations of a standard signal in the $^{19}$F NMR.

Figure 15:
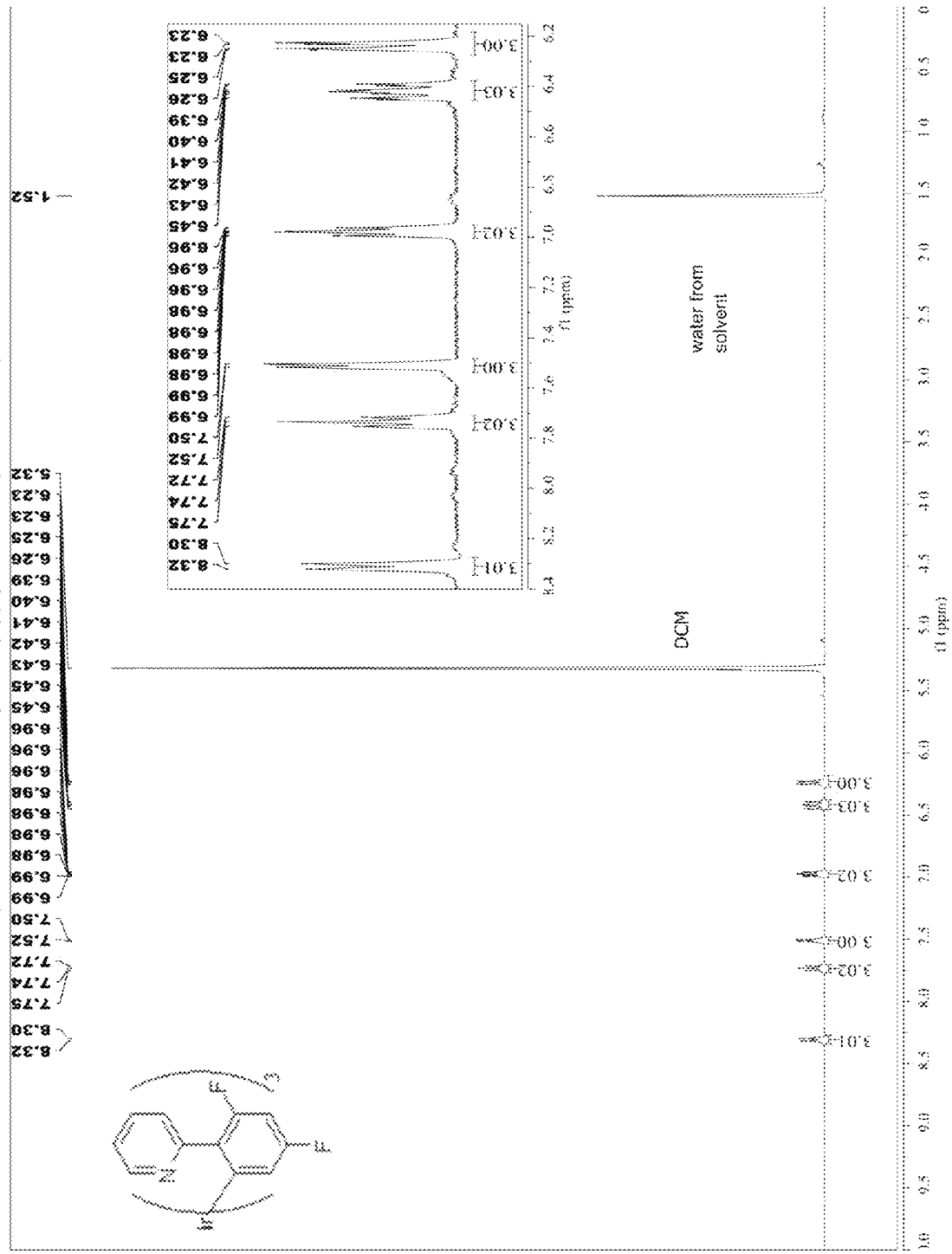
FIG. 15 contains $^1H$ NMR spectra of Fac-Tris(2-(4,6-difluorophenyl)pyridinato) iridium (III), as produced in Example 5.

FIG. 15—$^1$H NMR (400 MHz, Methylene Chloride-d2) δ 8.31 (d, J=8.3 Hz, 1H), 7.73 (t, J=7.8 Hz, 1H), 7.51 (d, J=5.4 Hz, 1H), 7.04-6.91 (m, 2H), 6.42 (ddd, J=11.7, 9.1, 2.5 Hz, 1H), 6.24 (dd, J=9.2, 2.4 Hz, 1H).

Figure 16:
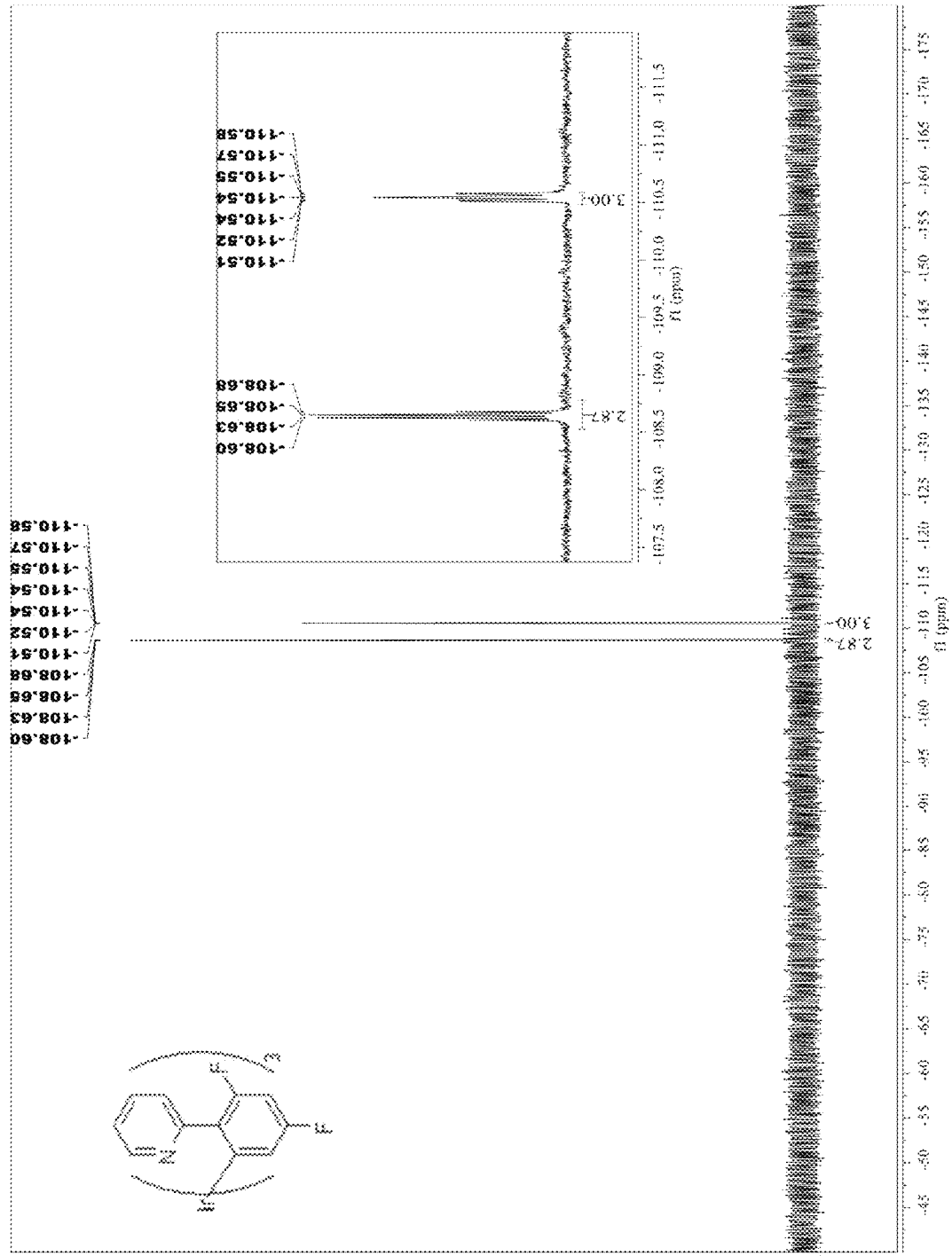
FIG. 16 contains $^{19}F$ NMR spectra of Fac-Tris(2-(4,6-difluorophenyl)pyridinato) iridium (III), as produced in Example 5.

FIG. 16—$^{19}$F NMR (376 MHz, Chloroform-d) δ −108.64 (q, J=9.2 Hz), −110.54 (ddd, J=13.0, 9.8, 2.6 Hz).

Figure 17:
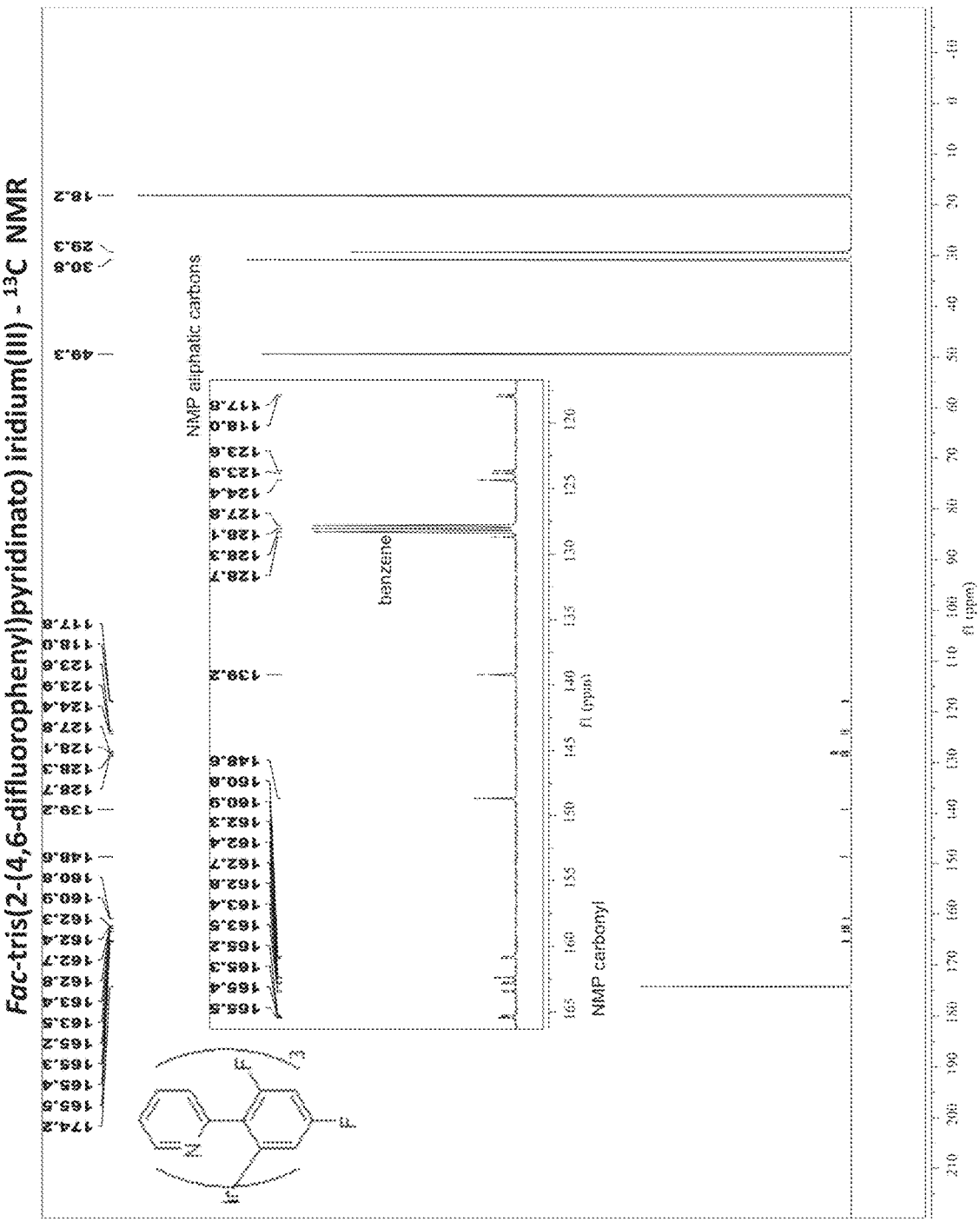
FIG. 17 contains $^{13}C$ NMR spectra of Fac-Tris(2-(4,6-difluorophenyl)pyridinato) iridium (III), as produced in Example 5.

FIG. 17—$^{13}$C NMR (101 MHz, Benzene-d6/NMP) δ 165.4 (d, J=5.6 Hz), 165.3 (d, J=11.7 Hz), 163.1 (dd, J=64.4, 11.8 Hz), 162.4 (d, J=6.8 Hz), 160.8 (d, J=12.7 Hz), 148.6, 139.2, 128.7, 124.4, 123.7 (d, J=20.8 Hz), 117.9 (d, J=16.3 Hz). FT-IR (neat) cm-1 3009, 1555, 1160, 786.

2-(4,6-Difluoro)phenylpyridine recovery: The previously retained aqueous layers were split equally between two 4 L Erlenmeyer flasks containing a 60 mm PTFE octagon stir bar. Each solution was stirred and slowly brought to pH 10 by adding 101 g of NaOH pellets. In two batches, each solution was added to a 6 L reparatory funnel, and the ligand was extracted from the salty water with DCM (6×800 mL). The combined organic extracts were added to a 20 L metal canister and were dried with 20 g of MgSO$_4$. After filtering the drying reagent through a 5 cm funnel with a cotton plug into another 20 L canister, the solvent was removed in batches by utilizing a continuous rotary evaporation setup (35° C., 130 mm Hg, 100 rpm) to afford 5.90 g, 96.8% yield of 2-(4,6-difluoro)phenylpyridine. The purity was determined to be 90.5% pure, compared to a standard signal (trimethoxybenzene) in the $^1$H NMR.

Figure 18:
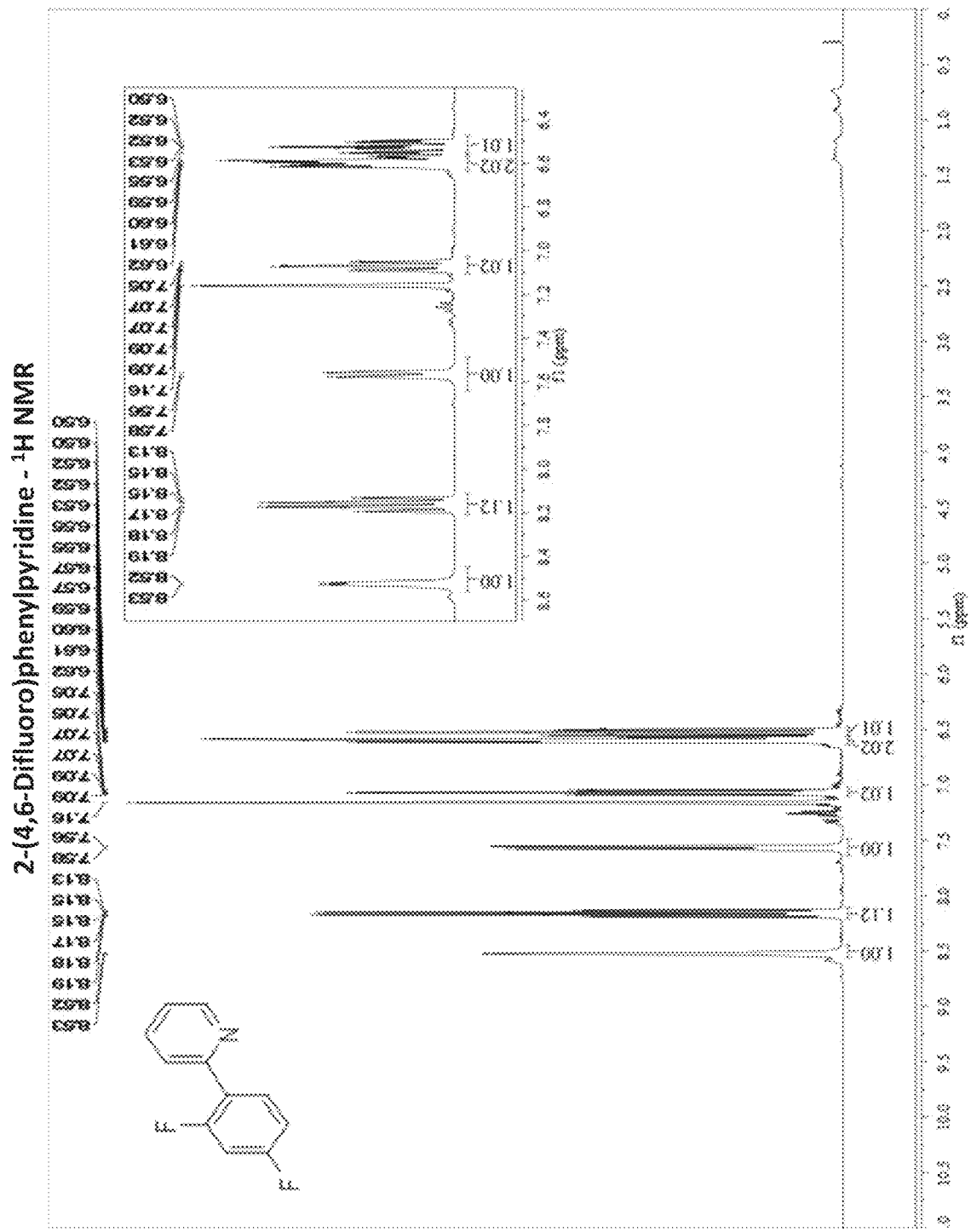
FIG. 18 contains $^1H$ NMR spectra of recovered ligand 2-(4,6-Difluoro)phenylpyridine, as recovered in Example 5.

FIG. 18—$^1$H NMR (400 MHz, Benzene-d6) δ 8.52 (d, J=4.0 Hz, 1H), 8.16 (td, J=8.9, 6.8 Hz, 1H), 7.57 (d, J=7.1 Hz, 1H), 7.07 (td, J=7.8, 1.8 Hz, 1H), 6.59 (td, J=7.9, 3.2 Hz, 2H), 6.52 (ddd, J=11.4, 8.8, 2.5 Hz, 1H).

Figure 19:
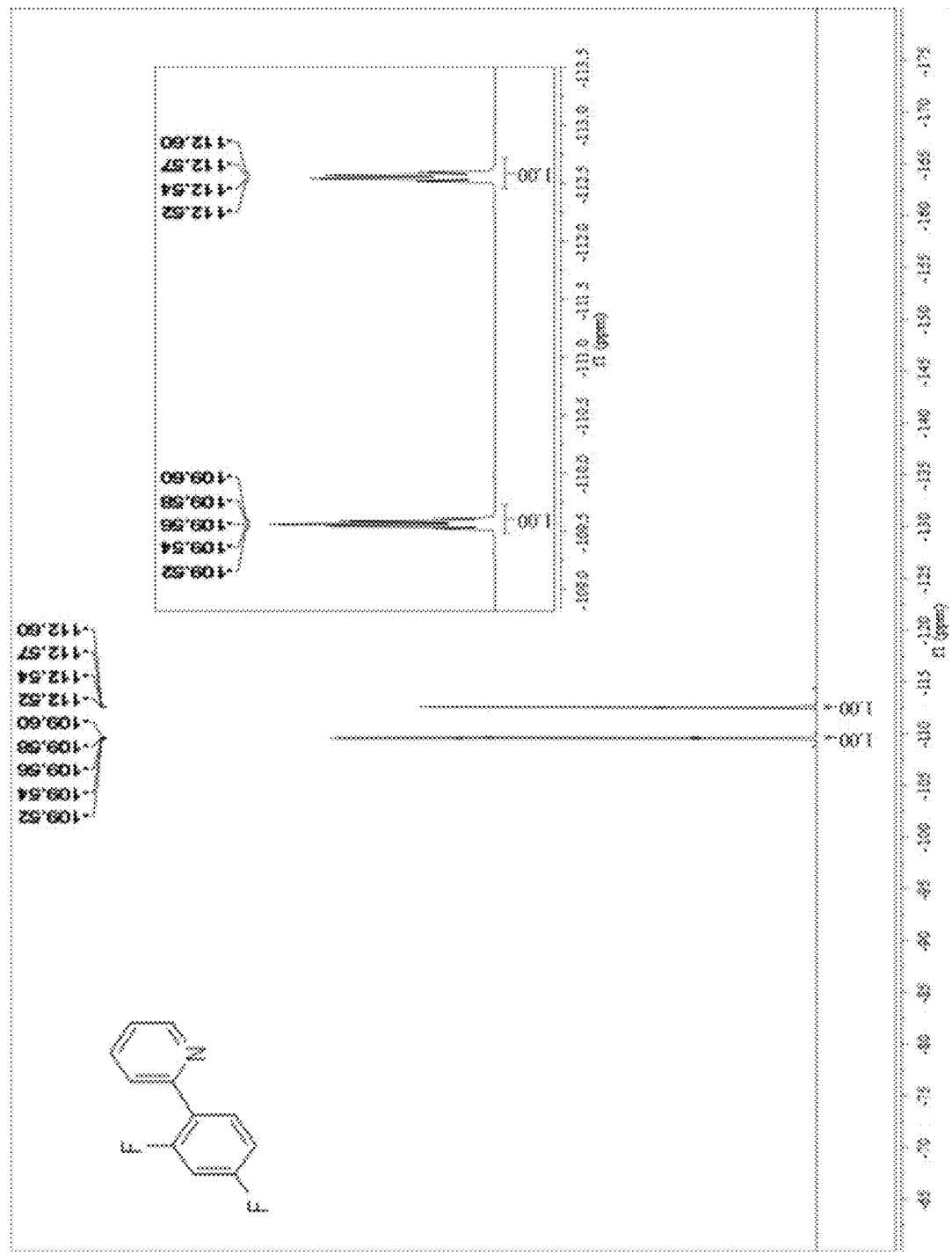
FIG. 19 contains $^{19}F$ NMR spectra of recovered ligand 2-(4,6-Difluoro)phenylpyridine, as recovered in Example 5.

FIG. 19—$^{19}$F NMR (376 MHz, Benzene-d6) δ −109.56 (p, J=8.3 Hz), −112.56 (q, J=10.7, 9.9 Hz).

Figure 20:
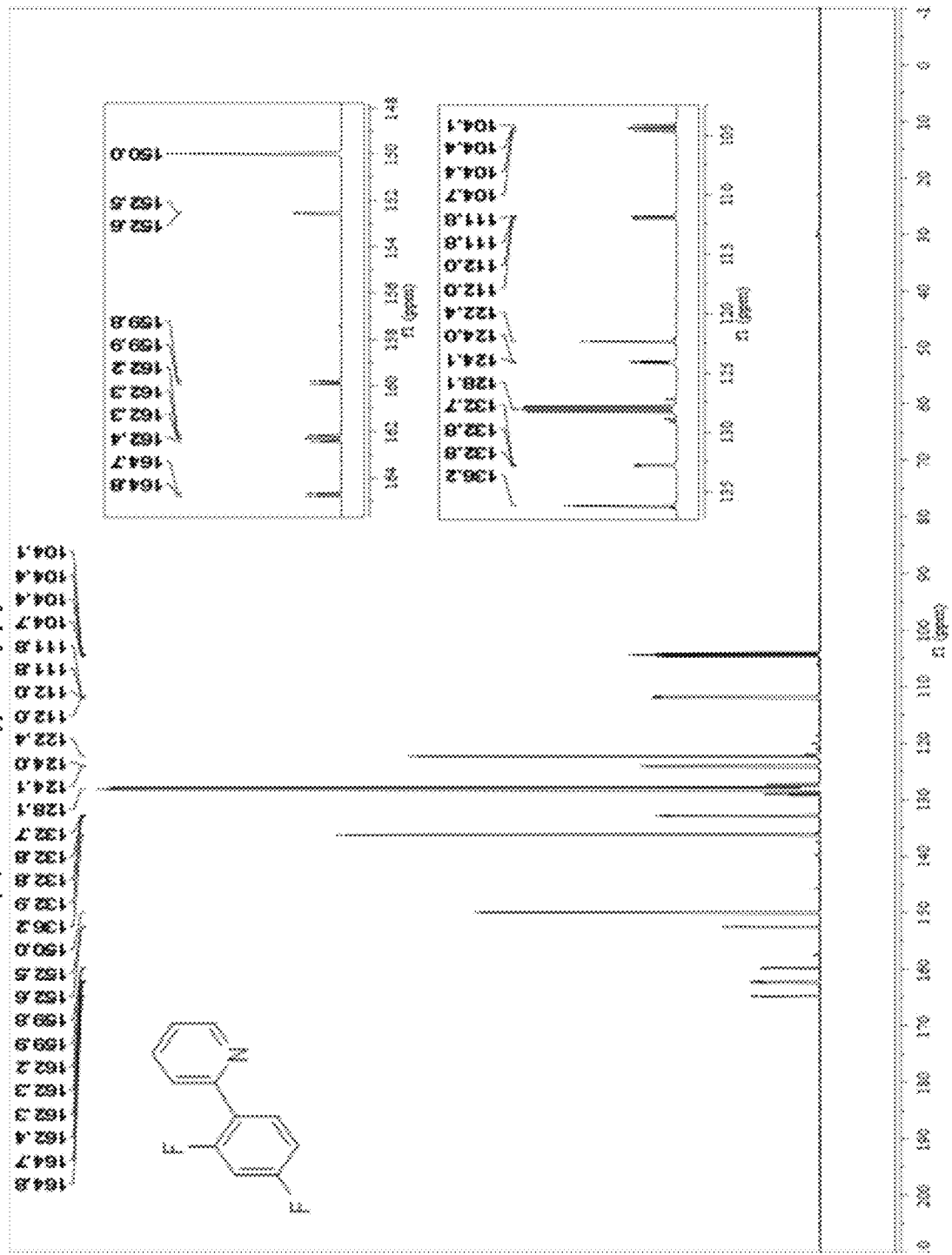
FIG. 20 contains $^{13}C$ NMR spectra of recovered ligand 2-(4,6-Difluoro)phenylpyridine, as recovered in Example 5.

FIG. 20—$^{13}$C NMR (101 MHz, Benzene-d6) δ 164.7 (d, J=12.1 Hz), 162.3 (dd, J=13.8, 12.0 Hz), 159.9 (d, J=11.9 Hz), 152.6 (d, J=2.7 Hz), 150.0, 136.2, 132.8 (dd, J=9.5, 4.6 Hz), 124.1 (d, J=11.0 Hz), 122.4, 111.9 (dd, J=21.0, 3.6 Hz), 104.4 (dd, J=27.3, 25.4 Hz). FT-IR (neat) cm$^{-1}$ 3086, 1567, 1138, 780.

Example 6

Figure 21:
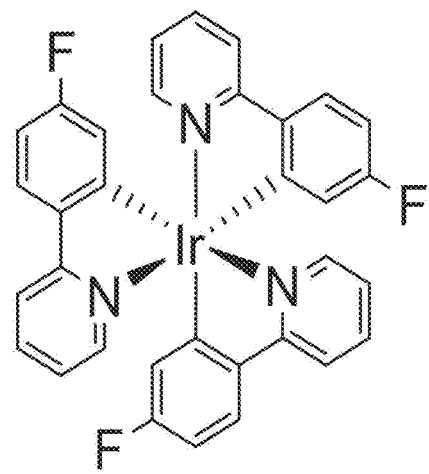
FIG. 21 illustrates the structure of photocatalyst Fac-Tris [5-fluoro-2-(2-pyridinyl-N)phenyl-C]iridium(III)), as produced in Example 6.

Synthesis of Fac-Tris[5-fluoro-2-(2-pyridinyl-N)phenyl-C]iridium(III)) Photocatalyst (FIG. 21)

Iridium (III) chloride anhydrous (0.47 g, 1.36 mmol, 1 equivalent), 2-(4-fluorophenyl)-pyridine (2.83 g, 16.4 mmol, 12.0 equivalents), and 0.41 L of DI water (0.003 M with respect to IrCl$_3$) were added to a 1 L Parr reactor. The reaction mixture was pressurized with argon (10.0 psi), stirred, and then depressurized three times, and finally charged again with argon before sealing. The reaction mixture was heated to 205° C. for 48 h. Then the reactor was cooled, and the reactor was opened after cooling, revealing an insoluble yellow solid on the surfaces and dispersed in the aqueous phase. All contents were transferred slowly to a 4 L separatory funnel aided by a large 5 cm glass funnel. Then the interior of the reactor was mechanically scraped (to extract the yellow material) with metal tongs, cotton balls, and 250 mL of dichloromethane (DCM) from a spray bottle, and again all contents were added to the separatory funnel.

While still in the funnel, the cotton was rinsed with 25 mL of DCM from a spray bottle and evenly pressed with tongs to release the yellow material from the cotton. After removing the cotton, the solution was then diluted with 1.0 L of DCM. The separatory funnel was shaken vigorously, allowed to settle and again shaken, and the organic layer was then slowly separated from the aqueous layer; the aqueous layer was further extracted with more DCM (3×10 mL), and the organic layers were combined. The aqueous layers were kept for future ligand recovery. The combined organic layer was washed with a 1 M HCl solution, with vigorous mixing prior to separation (3×500 mL). Each HCl wash was then back extracted with DCM (3×10 mL) to insure complete recovery of the product. After the final wash, the organic layer was filtered slowly (20 min) through a CELITE® (25 g) pad (Imerys Minerals California, Inc., San Jose, Calif.) on top of a 150 mL medium porosity sintered glass funnel, into a 3 L round-bottomed flask, and then dried with 30 g of MgSO$_4$. After filtering the drying reagent using a 4 L Erlenmeyer flask fitted with a 5 cm funnel/cotton plug, a homogenous aliquot was removed for NMR analysis. Finally, the solvent was removed in batches by transferring to a 2.5 L round-bottomed flask by rotary evaporation (35° C., 30 mm Hg, 150 rpm) to afford 963 mg (96%) of Ir(Fppy)$_3$ as a bright yellow solid.

Figure 22:
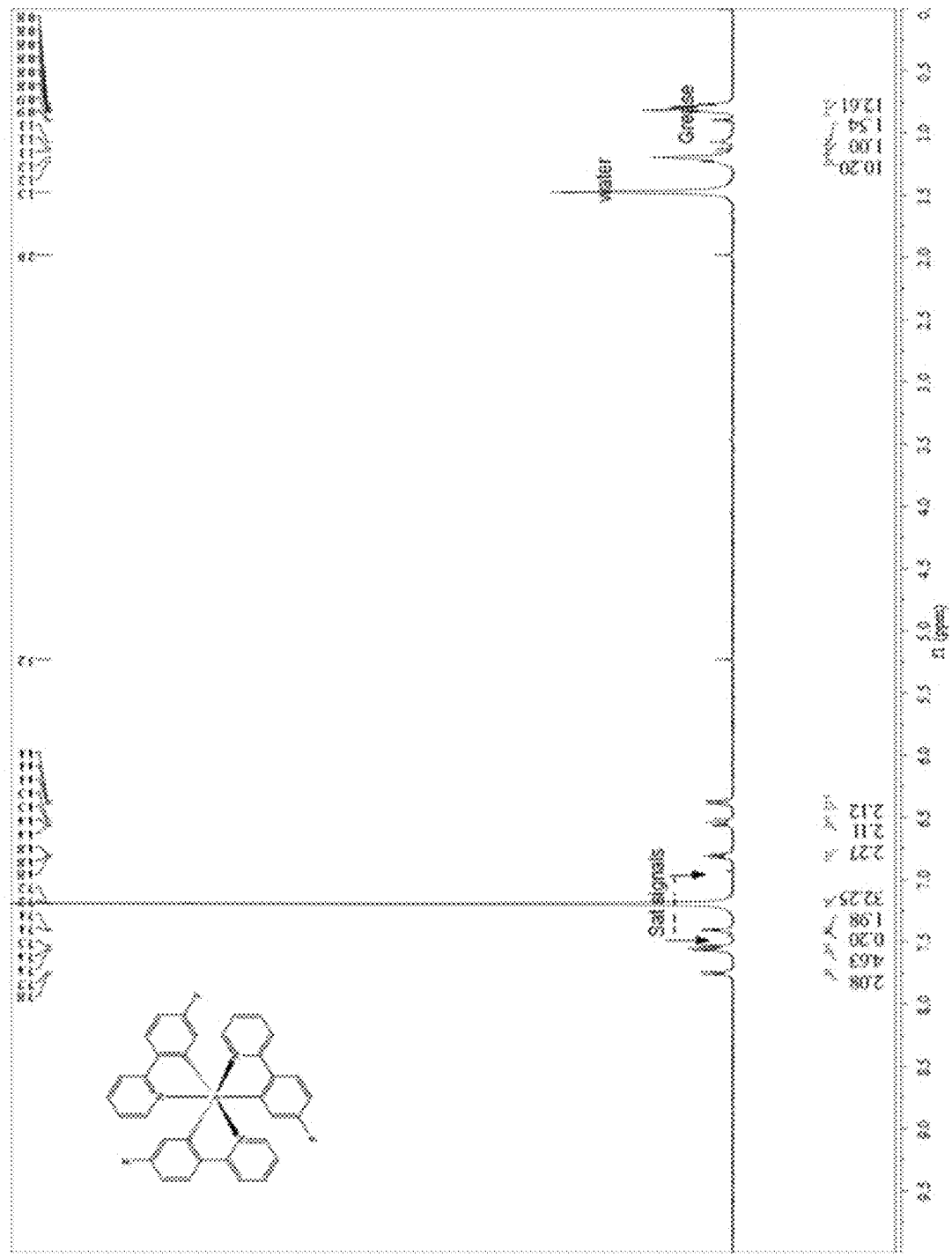
FIG. 22 contains $^1H$ NMR spectra of Fac-Tris[5-fluoro-2-(2-pyridinyl-N)phenyl-C]iridium(III)), as produced in Example 6.

FIG. 22—$^1$H NMR (Methylene Chloride-d2, 400 MHz): d δ 7.88 (d, 3H, J=8.2 Hz), 7.72-7.64 (m, 6H), 7.52 (ddd, 3H, J=5.5, 1.6, 0.8 Hz), 6.94 (ddd, 3H, J=7.1, 5.6, 1.3 Hz), 6.63 (td, 3H, J=8.7, 2.7 Hz), 6.39 (dd, 3H, J=10.3, 2.7 Hz) ppm. $^{13}$C NMR (Methylene Chloride-d2, 101 MHz): d δ 165.3 (d, J=5.4 Hz), 163.4 (d, J=5.7 Hz), 162.8, 147.2, 140.2, 136.6, 125.8 (d, J=9.2 Hz), 122.0, 121.8 (d, J=16.4 Hz), 118.9, 107.4 (d, J=23.6 Hz) ppm.

Figure 23:
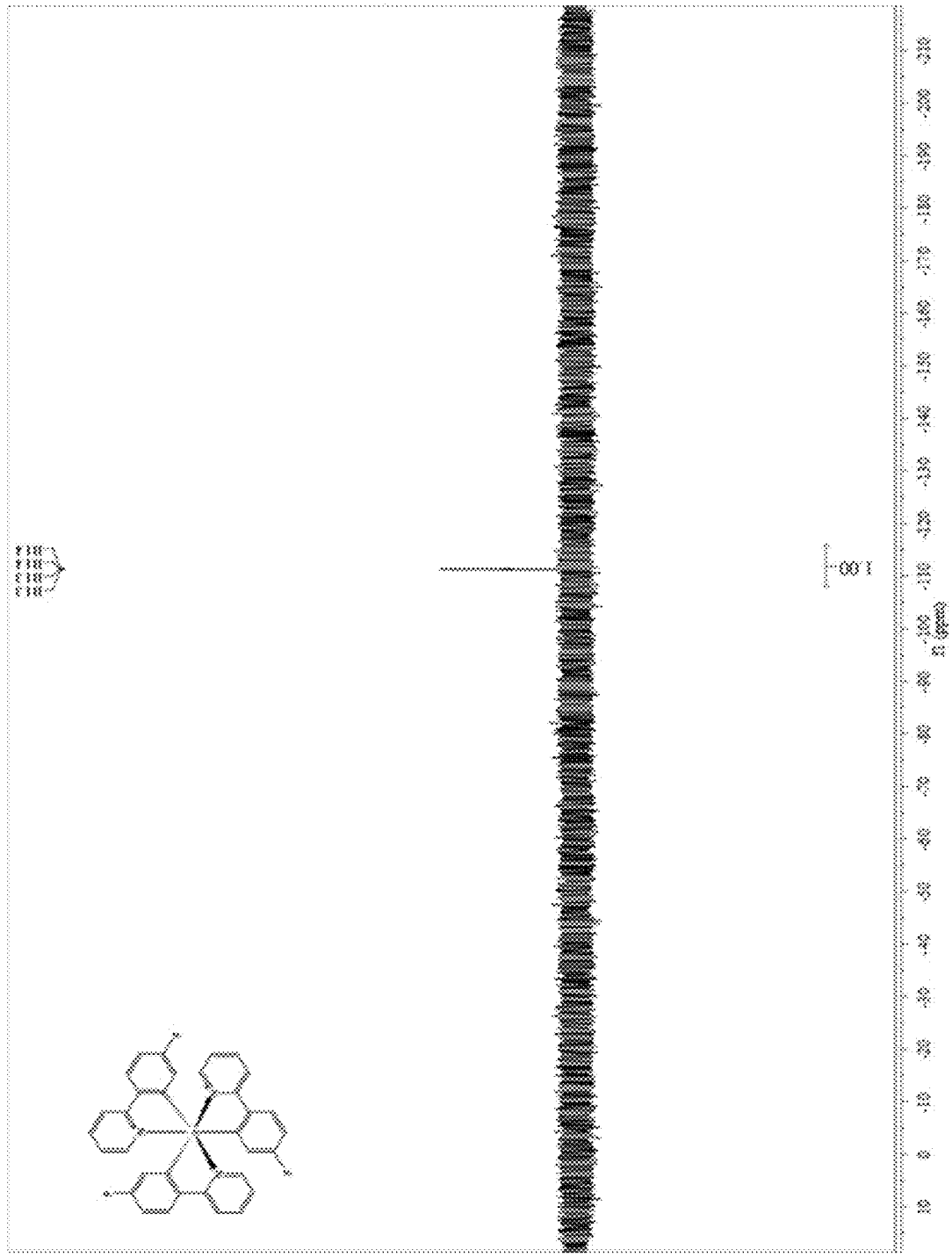
FIG. 23 contains $^{19}F$ NMR spectra of Fac-Tris[5-fluoro-2-(2-pyridinyl-N)phenyl-C]iridium(III)), as produced in Example 6.

FIG. 23—$^{19}$F NMR (376 MHz, Methylene Chloride d2) d 112.33 (ddd, J=10.3, 9.1, 5.7 Hz).

Recovery of 2-(4-fluorophenyl)-pyridine Ligand: The solution was stirred and slowly brought to pH 10 by adding 56 g of NaOH pellets in 10 portions. The solution was added to a 6 L separatory funnel, and the ligand was extracted from the salty water with DCM (4×900 mL). The combined organic extracts were added to a 20 L metal canister and were dried with 20 g of MgSO$_4$. After filtering the drying reagent through a 5 cm funnel with a cotton plug into another 20 L canister, the solvent was removed in batches by utilizing a continuous rotary evaporation setup (35° C., 130 mm Hg, 100 rpm) to afford 1.55 g, 73% (based on excess 9 equiv) of 2-phenylpyridine was recovered.

Example 7

Figure 24:
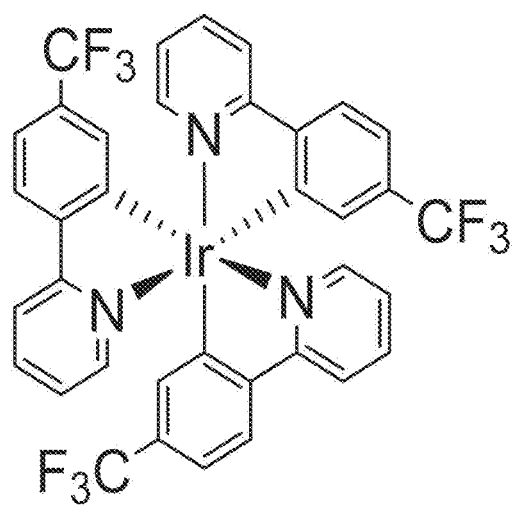
FIG. 24 illustrates the structure of photocatalyst Fac-Tris [2-(2-pyridinyl-N)-5-(trifluoromethyl)phenyl-C]iridium (III), as produced in Example 7.

Synthesis of Fac-Tris[2-(2-pyridinyl-N)-5-(trifluoromethyl)phenyl-C]iridium(III) Photocatalyst (FIG. 24)

Iridium (III) chloride anhydrous (1.16 g, 3.89 mmol, 1 equiv), 2-(4-trifluoromethyl phenyl)-pyridine (10.4 g, 46.6 mmol, 12.0 equiv), and 1.16 L of DI water (0.003 M with respect to IrCl$_3$) were added to a 1 L Parr reactor. The reaction mixture was pressurized with argon (10.0 psi), stirred, and then depressurized three times, and finally charged again with argon before sealing. The reaction mixture was heated to 205° C. for 48 h. Then the reactor was cooled, and the reactor was opened after cooling, revealing an insoluble yellow solid on the surfaces and dispersed in the aqueous phase. All contents were transferred slowly to a 4

L separatory funnel aided by a large 5 cm glass funnel. Then the interior of the reactor was mechanically scraped (to extract the yellow material) with metal tongs, cotton balls, and acetone (100 mL) was used to remove residual compound(s) from the Parr reactor and transferred to a different 250 mL round bottom flask and concentrated down.

The solid was placed on a filter frit and washed with 1 M HCl to wash away ligand. Yellow solid from the frit was taken into 200 mL of acetone and dry loaded with 40 g of silica and column ran with 5-6 column volumes to separate remaining ligand. The column was then run with 60:40 Hexanes:EtOAc to pull of dimer, and then the solvent system was switched to 100% DCM to recover the catalyst as a yellow solid in 67.58% yield, 2.26 g.

Figure 25:
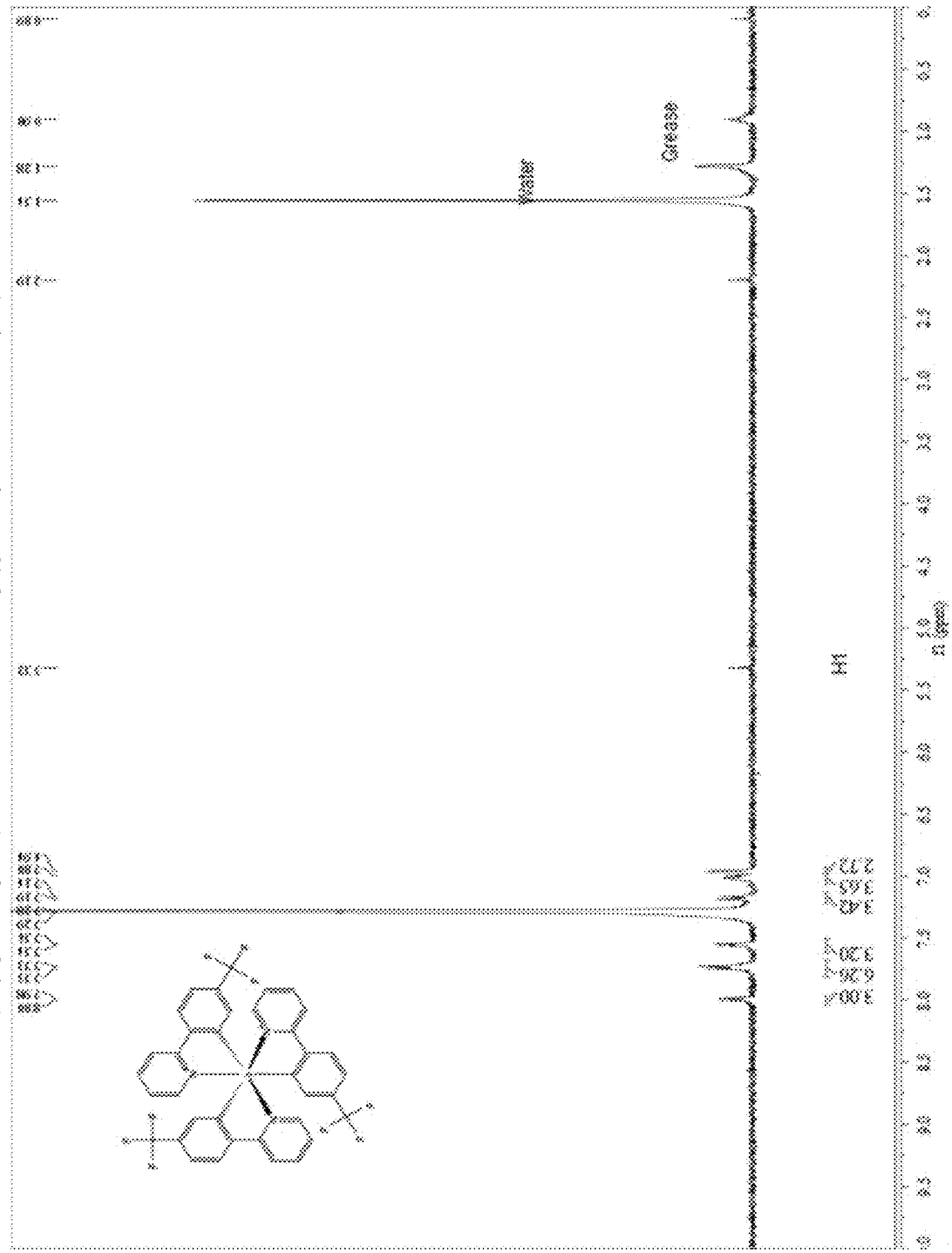
FIG. 25 contains $^1H$ NMR spectra of Fac-Tris[2-(2-pyridinyl-N)-5-(trifluoromethyl)phenyl-C]iridium(III), as produced in Example 7.

FIG. 25—$^1$H NMR(Chloroform-d, 400 MHz): δ=7.99 (d, 3H, J=8.3 Hz), 7.77-7.69 (m, 6H), 7.55 (dd, 6H, J=6.0, 1.3 Hz), 7.20-7.15 (m, 3H), 7.02 (ddd, 3H, J=7.1, 5.2, 1.1 Hz), 6.96 (b, 3H) ppm.

$^{13}$C NMR (Methylene Chloride-d2, 101 MHz): δ=165.0, 159.2, 147.5-147.4 (m), 147.3, 137.0.132.4 (m), 130.6, 123.9, 123.4, 120.0, 117.3-117.2 (m), 100.0.

Figure 26:
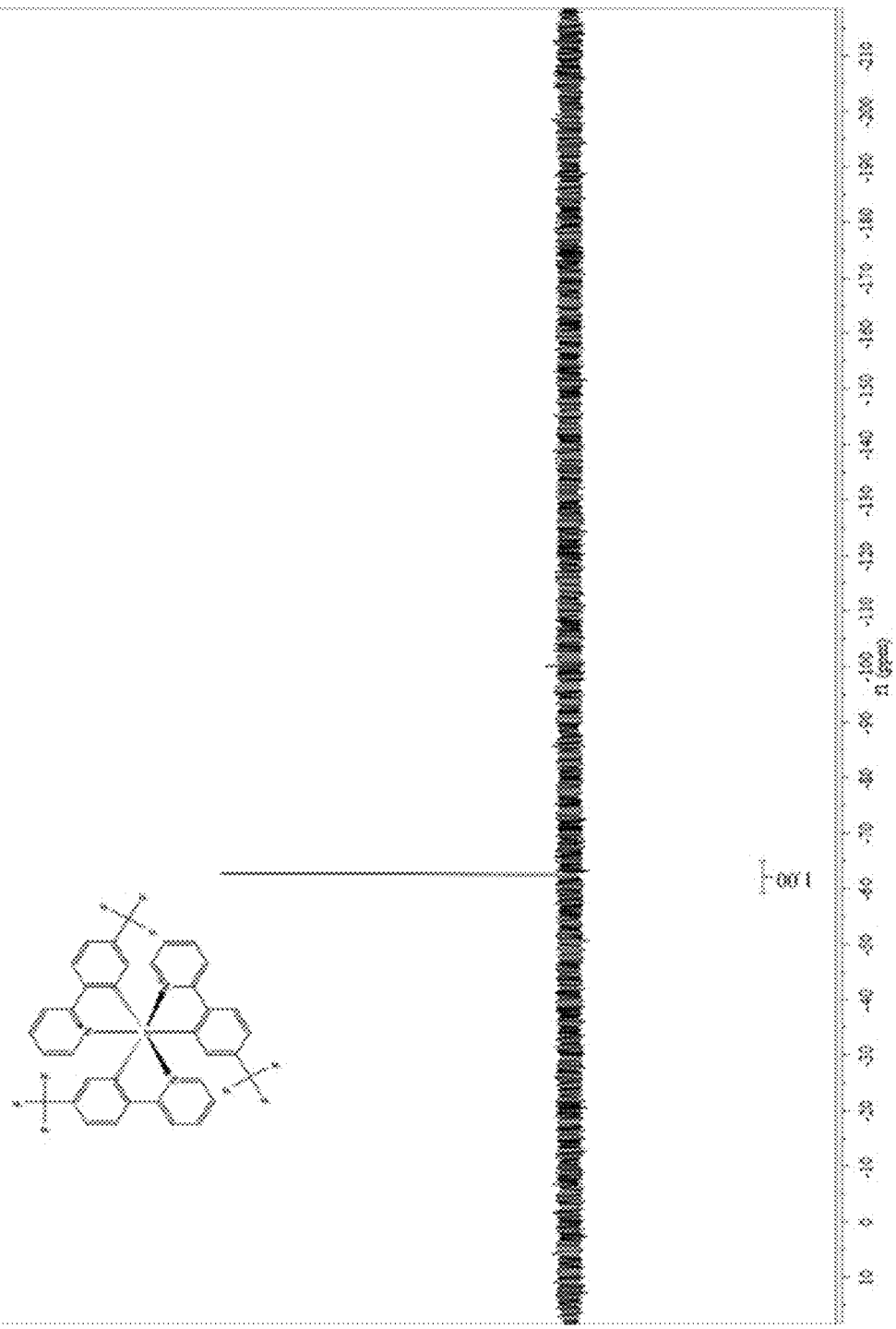
FIG. 26 contains $^{19}F$ NMR spectra of Fac-Tris[2-(2-pyridinyl-N)-5-(trifluoromethyl)phenyl-C]iridium(III), as produced in Example 7.

FIG. 26—$^{19}$F NMR (376 MHz, Chloroform-d) δ -62.76 (s). LC/MS (m/z) calculated for $C_{36}H_{21}F_9IrN_3$ 859.12 found M, 858.70.

Example 8

Recovery of Ligand

Figure 27:
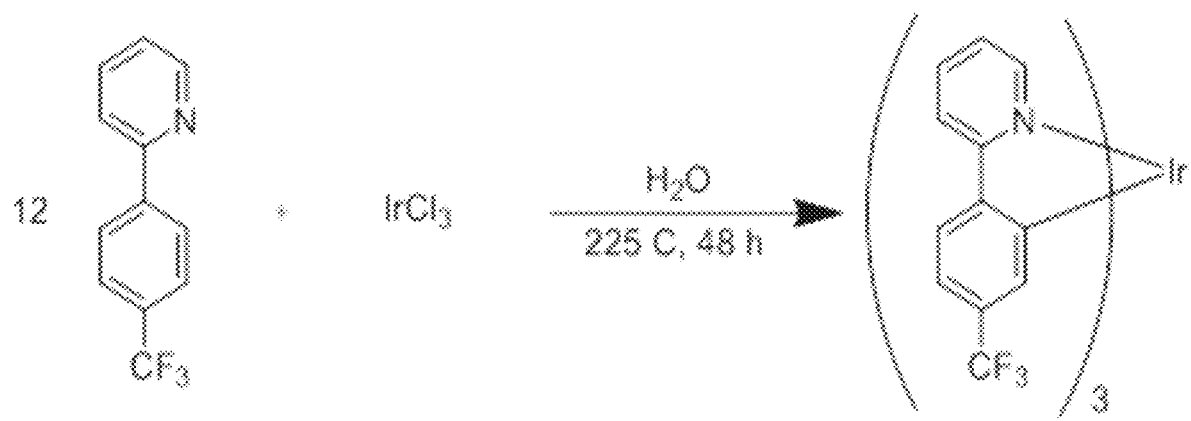
FIG. 27 illustrates another embodiment of the synthesis method of the present disclosure, as utilized in Example 8.

FIG. 27 illustrates a method for synthesizing Fac-Tris[2-(4-trifluoromethylphenyl)pyridinato] iridium (III). The method was carried out as described in the Examples above using a Parr reactor and with heating to 225° C. for 48 h. Upon cooling, the aqueous phase was filtered directly from the Parr reactor. The crude product was removed from the reactor and broken up, then allowed to stir in hexanes. The hexanes were filtered in frit (the porosity thereof was not important), and hexanes were added to the yellow solid until the filtrate was clear. The hexanes were removed via a rotovap until the remaining product was mostly a white solid. At this point, a sufficient amount of 1 M HCl to dissolve the solid was added, and this aqueous phase was washed with DCM to remove any yellow impurities. The aqueous phase was basified slowly (to a pH of about 12) and/or on ice (as ligand will readily co-distill with water). The white precipitate was then cold filtered to yield ligand (>99% via $^{19}$F NMR).

The yields for this example are as follows:
Theoretical Catalyst: 3.6472 g
Isolated Catalyst: 2.879 g
% Catalyst yield: 78.94%
Theoretical Ligand (w/78.94% Pdt Conversion): 9.13 g
Isolated Ligand: 5.9243 g
% Ligand Yield: 64.89%
Total catalyst to date: 9.75 g Example 9

Figure 28:
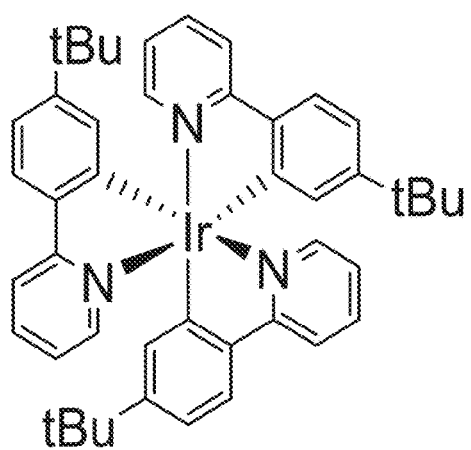
FIG. 28 illustrates the structure of photocatalyst Fac-Tris [2-(2-pyridinyl-N)-5-(tert-butyl)phenyl-C]iridium(III), as produced in Example 9.

Synthesis of Fac-Tris[2-(2-pyridinyl-N)-5-(tert-butyl)phenyl-C]iridium(III) Photocatalyst (FIG. 28)

Iridium (III) chloride anhydrous (0.118 g, 0.395 mmol, 1 equivalent), 2-(4-(tert-butyl)phenyl)pyridine (1.00 g, 4.74 mmol, 12.0 equivalents), and 0.118 L of DI water (0.003 M with respect to $IrCl_3$) were added to a 1 L Parr reactor. The reaction mixture was pressurized with argon (10.0 psi), stirred, and then depressurized three times, and finally charged again with argon before sealing. The reaction mixture was heated to 205° C. for 48 h. Then the reactor was cooled, and the reactor was opened after cooling, revealing an insoluble yellow solid on the surfaces and dispersed in the aqueous phase. All contents were transferred slowly to a 4 L separatory funnel aided by a large 5 cm glass funnel. Then the interior of the reactor was mechanically scraped (to extract the yellow material) with metal tongs, cotton balls, and 100 mL of dichloromethane (DCM) from a spray bottle, and again all contents were added to the separatory funnel.

While still in the funnel, the cotton was rinsed with 10 mL of DCM from a spray bottle and evenly pressed with tongs to release the yellow material from the cotton. After removing the cotton, the solution was then diluted with 250 mL of DCM. The separatory funnel was shaken vigorously, allowed to settle and again shaken, and the organic layer was then slowly separated from the aqueous layer; the aqueous layer was further extracted with more DCM (3×10 mL), and the organic layers were combined. After the final extraction, the organic layer was filtered slowly (20 min) through a CELITE® (25 g) pad (Imerys Minerals California, Inc., San Jose, Calif.) on top of a 150 mL medium porosity sintered glass funnel, into a 1 L round-bottomed flask, and then dried with 30 g of $MgSO_4$. After filtering the drying reagent using a 1 L Erlenmeyer flask fitted with a 5 cm funnel/cotton plug, a homogenous aliquot was removed for NMR analysis. The solvent was removed in batches by transferring to a 1 L round-bottomed flask by rotary evaporation, then the ligand was washed away with pentane (4×40 mL), affording 111 mg (34%) of Ir(5-tertbutyl-ppy)$_3$ as a bright orange/yellow solid.

Figure 29:
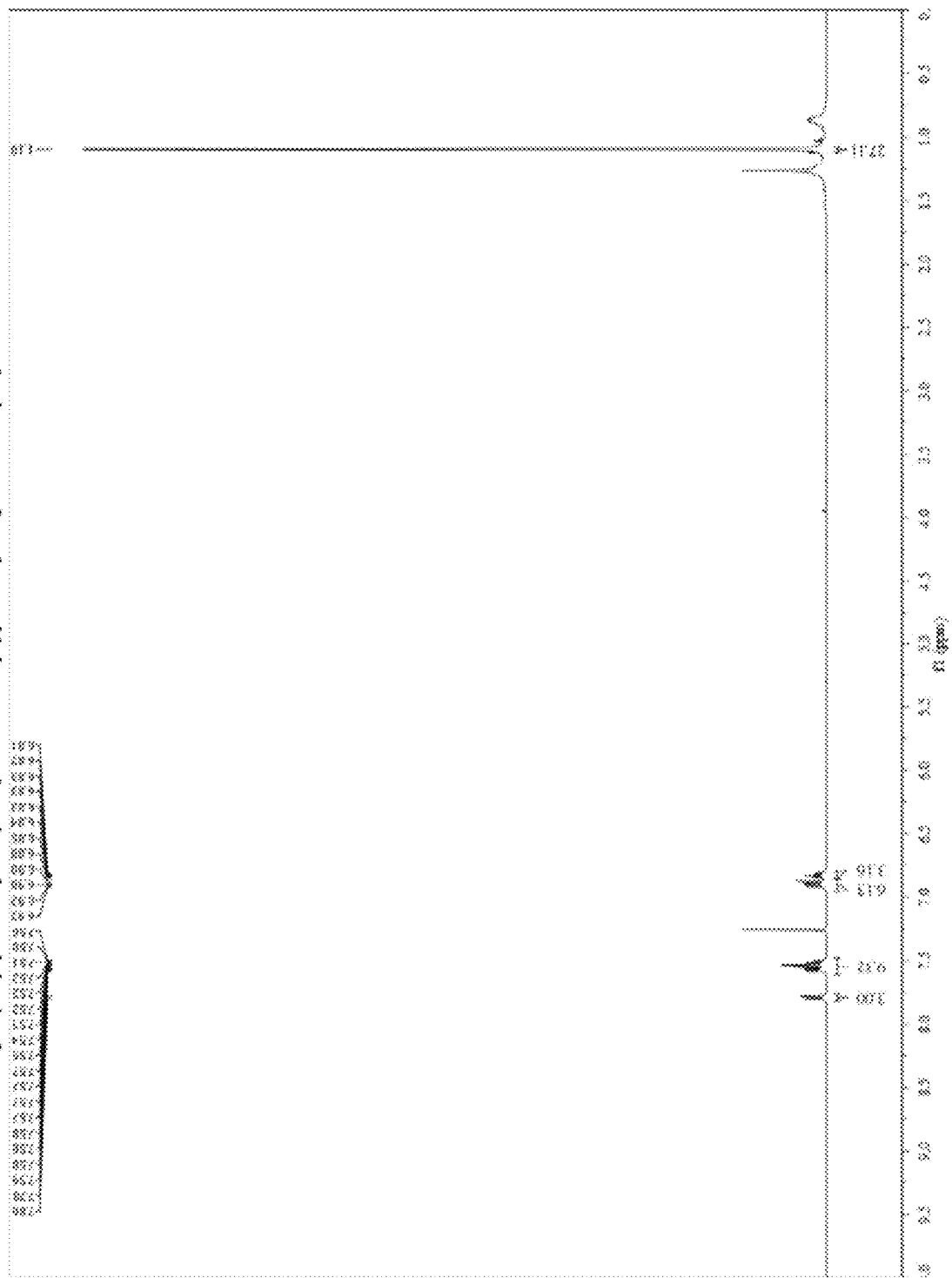
FIG. 29 contains $^1H$ NMR spectra of Fac-Tris[2-(2-pyridinyl-N)-5-(tert-butyl)phenyl-C]iridium(III), as produced in Example 9.

FIG. 29—$^1$H NMR (400 MHz, Chloroform-d) d 7.79 (d, 3H, J=8.2 Hz), 7.60-7.48 (m, 9H), 6.93-6.86 (m, 6H), 6.83 (ddd, 3H, J=7.0, 5.6, 1.1 Hz), 1.10 (s, 27H).

Figure 30:
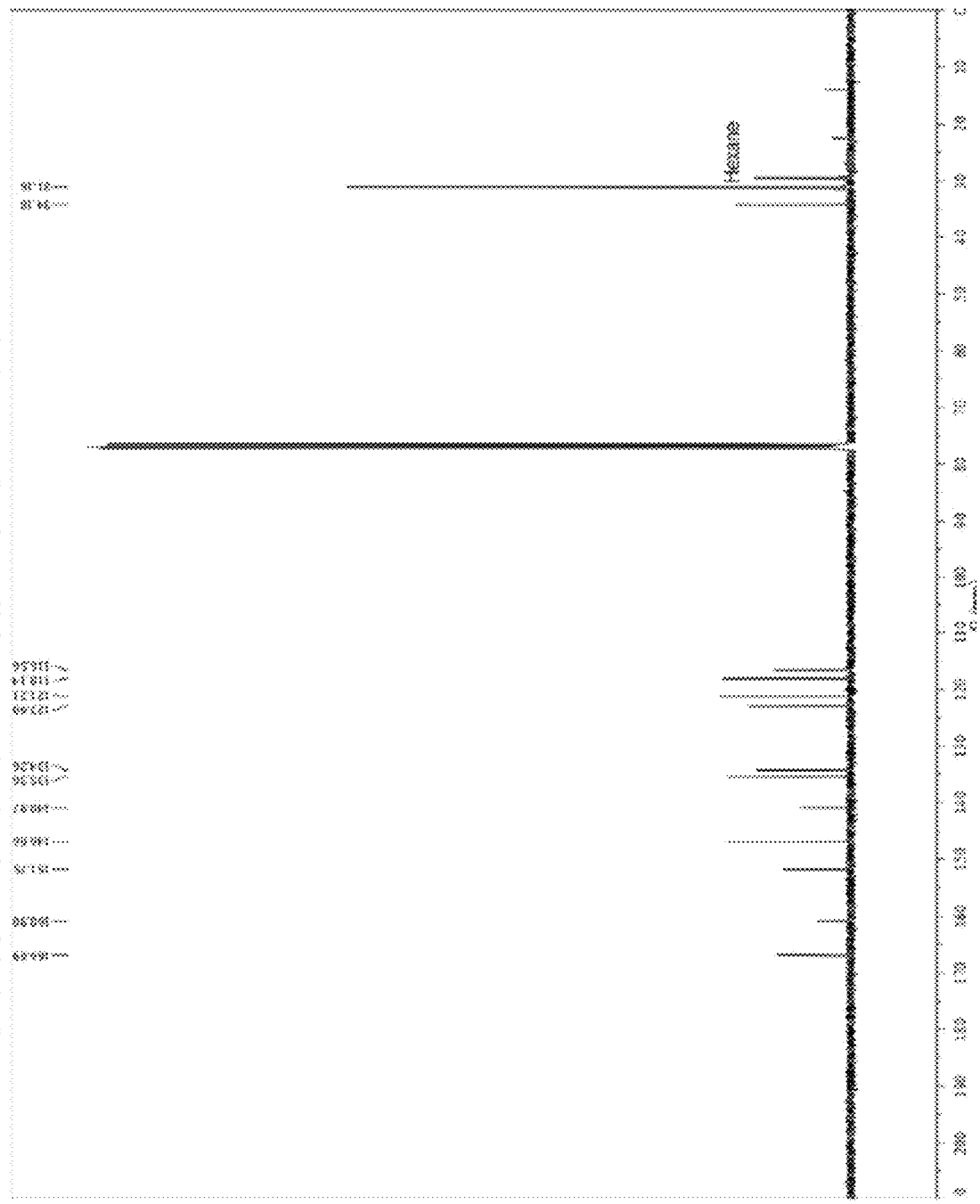
FIG. 30 contains $^{13}C$ NMR spectra of Fac-Tris[2-(2-pyridinyl-N)-5-(tert-butyl)phenyl-C]iridium(III), as produced in Example 9.

FIG. 30—$^{13}$C NMR (101 MHz, Chloroform-d) d 167.5, 161.5, 152.4, 147.5, 141.6, 136.0, 134.9, 123.5, 121.8, 118.8, 117.2, 34.8, 31.8.

Thus, in accordance with the present disclosure, there have been provided compositions, as well as methods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

REFERENCES

The following references, to the extent that they provide exemplary procedural or other details supplementary to those set forth herein, are specifically incorporated herein by reference. In addition, the following is not intended to be an Information Disclosure Statement; rather, an Information Disclosure Statement in accordance with the provisions of 37 CFR § 1.97 will be submitted separately.

Arora et al., *Organic Letters* (2015) 17:3722.
Cano-Yelo et al., *Journal of the Chemical Society*, Perkin Transactions (1984) 2:1093.
Chu et al., *J. Am. Chem. Soc.* (2014) 136:10886.
Dedeian et al., *J. Inorg. Chem.* (1991) 30:1685.
Devery et al., *J Chemical Science* (2015) 6:537.
Fukuzumi et al., *The Journal of Physical Chemistry* (1990) 94:722.

Kalyanasundaram et al., *Coordination Chemistry Reviews* (1998) 177:347.
King et al., *J. Am. Chem. Soc.* (1985) 107:1431.
Konno et al., *Chemistry Letters* (2003) 32:252.
Lalevee et al., *Chemistry—A European Journal* (2011) 17:15027.
Lee et al., *J Korean Phys. Soc.* (2007) 50:1722.
Lowry et al., *Chemistry—A European Journal* (2006) 12:7970.
Ischay et al., *J. Am. Chem. Soc.* (2008) 130:12886.
McCusker, *Accounts of Chemical Research* (2003) 36:876.
McDonald et al., *Inorganic Chemistry* (2008) 47:6681.
Narayanam et al., *J. Chem. Soc. Reviews* (2011) 40:102.
Nguyen et al., *Nat. Chem.* (2012) 4:854.
Nicewicz et al., *Science* (2008) 322:77.
Pac et al., *J. Am. Chem. Soc.* (1981) 103:6495.
Prier et al., *Chem. Rev.* (2013) 113:5322.
Senaweera et al., *J. Am. Chem. Soc.* (2014) 136:3002.
Singh et al., *Chemical Science* (2015).
Singh et al., *Organic letters* (2013) 15:5390.
Singh et al., *J. Am. Chem. Soc.* (2014) 136:5275.
Singh et al., *Journal of Organometallic Chemistry* (2015) 776:51.
Tamayo et al., *J. Am. Chem. Soc.* (2003) 125:7377.
Terrett et al., *J. Am. Chem. Soc.* (2014) 136:6858.
Tsuboyarna et al., *J. Am. Chem. Soc.* (2003) 125:12971.
Wallentin et al., *J. Am. Chem. Soc.* (2012) 134:8875.
Weaver et al., *Tetrahedron* (2014) 70:7413.
Zuo et al., *J. Am. Chem. Soc.* (2014) 136:5257.

What is claimed is:

1. A method of synthesizing and isolating a facial-tris-homoleptic phenylpyridinato iridium (III) photocatalyst and recovering excess 2-phenylpyridine ligand from said synthesis, the method further comprising the steps of:
    (a) charging a reactor with $IrCl_3*nH_2O$ and a 2-phenylpyridine ligand to form a reaction mixture;
    (b) pressurizing the reaction mixture with inert gas;
    (c) heating the reaction mixture for a sufficient amount of time to synthesize a fac-tris-homoleptic phenylpyridinato iridium (III) photocatalyst;
    (d) cooling the reaction mixture;
    (e) removing the reaction mixture from the reactor, wherein the reaction mixture comprises a solid material and an aqueous phase; and
    (f) isolating the fac-tris-homoleptic phenylpyridinato iridium (III) photocatalyst from the reaction mixture, wherein the isolation process comprises performing two or more of steps (I)-(VI):
        (I) contacting the reaction mixture with an organic solvent;
        (II) extracting the fac-tris-homoleptic phenylpyridinato iridium (III) photocatalyst into the organic solvent;
        (III) separating at least a portion of an organic phase from an aqueous phase;
        (IV) filtering the separated organic phase; and
        (V) drying the separated organic phase containing the fac-tris-homoleptic phenylpyridinato iridium (III) photocatalyst to form a drying reagent; and
        (VI) removing organic solvent from the drying reagent; and
    wherein the fac-tris-homoleptic phenylpyridinato iridium (III) photocatalyst is isolated with a purity of at least about 90%, and wherein the at least about 90% purity of the photocatalyst is obtained in the absence of any chromatography steps; and
    (g) recovering excess 2-phenylpyridine ligand, wherein the recovery process comprises performing two or more of steps (i)-(vii):
        (i) basifying the aqueous phase separated in (III) to a pH wherein at least a portion of excess 2-phenylpyridine separates out of the aqueous phase, wherein the aqueous phase is basified using a solid base;
        (ii) contacting the reaction mixture of (i) with an organic solvent;
        (iii) extracting the 2-phenylpyridine ligand into the organic solvent;
        (iv) separating at least a portion of an organic phase from an aqueous phase;
        (v) filtering the separated organic phase; and
        (vi) drying the separated organic phase containing excess 2-phenylpyridine ligand to form a drying reagent; and
        (vii) removing organic solvent from the drying reagent to isolate excess 2-phenylpyridine ligand; and
    wherein the excess 2-phenylpyridine ligand is recovered in a yield of at least about 40%.

2. The method of claim 1, wherein the solid base comprises NaOH pellets.

3. The method of claim 1, wherein in step (g)(i), the aqueous phase is basified to a pH in a range of from about pH 10 to about pH 12.

4. The method of claim 1, wherein at least about 1 gram of fac-tris-homoleptic phenylpyridinato iridium (III) photocatalyst is isolated.

5. The method of claim 1, wherein the isolation process of step (f) is further defined as comprising performing all of steps (I)-(VI).

6. The method of claim 1, wherein the recovery process of step (g) is further defined as comprising performing all of steps (i)-(vii).

7. The method of claim 1, wherein 1 equivalent of $IrCl_3*nH_2O$ is reacted with 12 equivalents of the 2-phenylpyridine ligand.

8. The method of claim 1, wherein the isolation process of step (f) is further defined as comprising performing two or more of steps (I)-(VII), wherein:
    (VII) selectively extracting impurities from the drying reagent of (VI) by washing with an organic solvent.

9. A method of synthesizing and isolating a facial-tris-homoleptic phenylpyridinato iridium (III) photocatalyst and recovering excess 2-phenylpyridine ligand from said synthesis, the method further comprising the steps of:
    (a) charging a reactor with $IrCl_3*nH_2O$ and a 2-phenylpyridine ligand to form a reaction mixture;
    (b) pressurizing the reaction mixture with inert gas;
    (c) heating the reaction mixture for a sufficient amount of time to synthesize a fac-tris-homoleptic phenylpyridinato iridium (III) photocatalyst;
    (d) cooling the reaction mixture;
    (e) removing the reaction mixture from the reactor, wherein the reaction mixture comprises a solid material and an aqueous phase; and
    (f) isolating the fac-tris-homoleptic phenylpyridinato iridium (III) photocatalyst from the reaction mixture, wherein the isolation process comprises performing two or more of steps (I)-(VI):
        (I) contacting the reaction mixture with an organic solvent;
        (II) extracting the fac-tris-homoleptic phenylpyridinato iridium (III) photocatalyst into the organic solvent;
        (III) separating at least a portion of an organic phase from an aqueous phase;

(IV) filtering the separated organic phase; and
(V) drying the separated organic phase containing the fac-tris-homoleptic phenylpyridinato iridium (III) photocatalyst to form a drying reagent; and
(VI) removing organic solvent from the drying reagent; and
wherein the fac-tris-homoleptic phenylpyridinato iridium (III) photocatalyst is isolated with a purity of at least about 90%, and wherein the at least about 90% purity of the photocatalyst is obtained in the absence of any chromatography steps; and
(g) recovering excess 2-phenylpyridine ligand, wherein the recovery process comprises performing two or more of steps (i)-(vii):
(i) basifying the aqueous phase separated in (III) to a pH in a range of from about pH 10 to about pH 12, wherein at least a portion of excess 2-phenylpyridine separates out of the aqueous phase;
(ii) contacting the reaction mixture of (i) with an organic solvent;
(iii) extracting the 2-phenylpyridine ligand into the organic solvent;
(iv) separating at least a portion of an organic phase from an aqueous phase;
(v) filtering the separated organic phase; and
(vi) drying the separated organic phase containing excess 2-phenylpyridine ligand to form a drying reagent; and
(vii) removing organic solvent from the drying reagent to isolate excess 2-phenylpyridine ligand; and
wherein the excess 2-phenylpyridine ligand is recovered in a yield of at least about 40%.

10. The method of claim 9, wherein at least about 1 gram of fac-tris-homoleptic phenylpyridinato iridium (III) photocatalyst is isolated.

11. The method of claim 9, wherein the isolation process of step (f) is further defined as comprising performing all of steps (I)-(VI).

12. The method of claim 9, wherein the recovery process of step (g) is further defined as comprising performing all of steps (i)-(vii).

13. The method of claim 9, wherein 1 equivalent of $IrCl_3 \cdot nH_2O$ is reacted with 12 equivalents of the 2-phenylpyridine ligand.

14. The method of claim 9, wherein the isolation process of step (f) is further defined as comprising performing two or more of steps (I)-(VII), wherein:
(VII) selectively extracting impurities from the drying reagent of (VI) by washing with an organic solvent.

15. A method of synthesizing and isolating a facial-tris-homoleptic phenylpyridinato iridium (III) photocatalyst and recovering excess 2-phenylpyridine ligand from said synthesis, the method further comprising the steps of:
(a) charging a reactor with $IrCl_3 \cdot nH_2O$ and a 2-phenylpyridine ligand to form a reaction mixture;
(b) pressurizing the reaction mixture with inert gas;
(c) heating the reaction mixture for a sufficient amount of time to synthesize a fac-tris-homoleptic phenylpyridinato iridium (III) photocatalyst;
(d) cooling the reaction mixture;
(e) removing the reaction mixture from the reactor, wherein the reaction mixture comprises a solid material and an aqueous phase; and
(f) isolating the fac-tris-homoleptic phenylpyridinato iridium (III) photocatalyst from the reaction mixture, wherein the isolation process comprises performing two or more of steps (I)-(VI):
(I) contacting the reaction mixture with an organic solvent;
(II) extracting the fac-tris-homoleptic phenylpyridinato iridium (III) photocatalyst into the organic solvent;
(III) separating at least a portion of an organic phase from an aqueous phase;
(IV) filtering the separated organic phase; and
(V) drying the separated organic phase containing the fac-tris-homoleptic phenylpyridinato iridium (III) photocatalyst to form a drying reagent; and
(VI) removing organic solvent from the drying reagent; and
wherein the fac-tris-homoleptic phenylpyridinato iridium (III) photocatalyst is isolated with a purity of at least about 90%, and wherein the at least about 90% purity of the photocatalyst is obtained in the absence of any chromatography steps; and
(g) recovering excess 2-phenylpyridine ligand, wherein the recovery process comprises performing steps (i)-(vii):
(i) basifying the aqueous phase separated in (III) to a pH wherein at least a portion of excess 2-phenylpyridine separates out of the aqueous phase;
(ii) contacting the reaction mixture of (i) with an organic solvent;
(iii) extracting the 2-phenylpyridine ligand into the organic solvent;
(iv) separating at least a portion of an organic phase from an aqueous phase;
(v) filtering the separated organic phase; and
(vi) drying the separated organic phase containing excess 2-phenylpyridine ligand to form a drying reagent; and
(vii) removing organic solvent from the drying reagent to isolate excess 2-phenylpyridine ligand; and
wherein the excess 2-phenylpyridine ligand is recovered in a yield of at least about 40%.

16. The method of claim 15, wherein in step (g)(i), the aqueous phase is basified to a pH in a range of from about pH 10 to about pH 12.

17. The method of claim 15, wherein at least about 1 gram of fac-tris-homoleptic phenylpyridinato iridium (III) photocatalyst is isolated.

18. The method of claim 15, wherein the isolation process of step (f) is further defined as comprising performing all of steps (I)-(VI).

19. The method of claim 15, wherein 1 equivalent of $IrCl_3 \cdot nH_2O$ is reacted with 12 equivalents of the 2-phenylpyridine ligand.

20. The method of claim 15, wherein the isolation process of step (f) is further defined as comprising performing two or more of steps (I)-(VII), wherein:
(VII) selectively extracting impurities from the drying reagent of (VI) by washing with an organic solvent.

* * * * *

UNITED STATES PATENT AND TRADEMARK OFFICE
CERTIFICATE OF CORRECTION

PATENT NO. : 11,014,078 B2
APPLICATION NO. : 16/491710
DATED : May 25, 2021
INVENTOR(S) : Jimmie Dean Weaver and Kip Allen Teegardin Page 1 of 1

It is certified that error appears in the above-identified patent and that said Letters Patent is hereby corrected as shown below:

In the Specification

Column 3, Line 40: Delete "reparatory" and replace with -- separatory --

Column 15, Line 50: Delete "reparatory" and replace with -- separatory --

Column 16, Line 58: Delete "reparatory" and replace with -- separatory --

Column 18, Line 33: Delete "reparatory" and replace with -- separatory --

Column 19, Line 29: Delete "reparatory" and replace with -- separatory --

Column 21, Line 25: Delete "reparatory" and replace with -- separatory --

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*